US012622906B2

(12) United States Patent
Wu et al.

(10) Patent No.: US 12,622,906 B2
(45) Date of Patent: May 12, 2026

(54) TREATMENT AND PROGNOSIS OF PANCREATIC CANCER

(71) Applicant: Cambridge Enterprise Limited, Cambridge (GB)

(72) Inventors: Tony James Wu, Cambridge (GB); Michael Gill, Cambridge (GB); Martin Miller, Cambridge (GB); Oliver Cast, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 846 days.

(21) Appl. No.: 17/785,790

(22) PCT Filed: Dec. 18, 2020

(86) PCT No.: PCT/GB2020/053295

§ 371 (c)(1),
(2) Date: Jun. 15, 2022

(87) PCT Pub. No.: WO2021/123813

PCT Pub. Date: Jun. 24, 2021

(65) Prior Publication Data

US 2023/0064214 A1 Mar. 2, 2023

(30) Foreign Application Priority Data

Dec. 18, 2019 (GB) ..................................... 1918692

(51) Int. Cl.

| | |
|---|---|
| ***A61K 31/506*** | (2006.01) |
| ***A61K 31/7068*** | (2006.01) |
| ***A61P 35/00*** | (2006.01) |
| ***G01N 33/574*** | (2006.01) |

(52) U.S. Cl.

CPC ........ *A61K 31/506* (2013.01); *A61K 31/7068* (2013.01); *A61P 35/00* (2018.01); *G01N 33/57484* (2013.01); *G01N 2800/52* (2013.01)

(58) Field of Classification Search

CPC .. A61K 31/506; A61K 31/7068; A61K 45/00; A61P 35/00; G01N 33/57484

See application file for complete search history.

(56) References Cited

U.S. PATENT DOCUMENTS

| | | | | |
|---|---|---|---|---|
| 2009/0286823 | A1 | 11/2009 | Veiby et al. | |
| 2013/0280254 | A1 | 10/2013 | Pollard | |
| 2017/0290808 | A1* | 10/2017 | Charo ............... | A61K 31/4192 |

OTHER PUBLICATIONS

Shankland, et al.; The Lancet, v380, Iss.9894, pp. 848-857; 2012 (Year: 2012).*

Cheng, Y. and Tian, H.; Molecules, v22, article 1551, pp. 1-20; 2017 (Year: 2017).*

Pancreatic Cancer Action Network, https://pancan.org/facing-pancreatic-cancer/diagnosis/staging/stage-4/, obtained from the internet Apr. 21, 2025, Internet Archive Wayback Machine Date Oct. 22, 2019 (Year: 2019).*

Argyle, et al.; Frontiers in Immunology, v9, Article 2629, pp. 1-15; 2018 (Year: 2018).*

Pevida M et al: "The chemokine CCL5 induces CCR1-mediated hyperalgesia in mice inoculated with NCTC 2472 tumoral cells," Neuroscience, New York, NY, US, vol. 259, Dec. 4, 2013 (Dec. 4, 2013, pp. 113-125, XP028817512, ISSN: 0306-4522, DOI: 10.1016/J.NEUROSCIENCE.2013.11.055 abstract.

Zhang et al. "Regulatory T-cell depletion alters the tumor microenvironment and accelerates pancreatic carcinogenesis." Cancer Discovery, vol. 10, No. 3, 2020, pp. 423-439 [available via https://cancerdiscovery.aacrjournals.org/content/10/3/422] See whole document especially section on pp. 431-432 titled "CCR1 inhibition recuses Treg depletion-induced PanIN progression.".

Yoshihara et al, Inferring tumour purity and stromal and immune cell admixture from expression data (ESTIMATE), Nature Comm., 2013, 4(2612), 1-11.

Shugang, Wei et al. Prognostic Value of SMAD4 in Pancreatic Cancer: A Meta-Analysis, Transl Oncol. 2016, 9(1), 1-7.

Cheng and Tian, Current development status of MEK inhibitors, Molecules, 2017, 22(10), 1551.

International Search Report and Written Opinion mailed on Mar. 12, 2021 in the corresponding International application No. PCT/GB2020/053295.

Search Report dated Jun. 8, 2020 issued in the priority United Kingdom application No. GB 1918692.3.

* cited by examiner

*Primary Examiner* — Jeffrey S Lundgren
*Assistant Examiner* — W. Justin Youngblood
(74) *Attorney, Agent, or Firm* — Jon E. Gordon; Haug Partners LLP

(57) ABSTRACT

The invention provides a CCR1 antagonist, or a pharmaceutically acceptable salt, hydrate or solvate thereof, for use in the treatment of pancreatic cancer, in particular a CCR1 antagonist, for example in combination with one or more further therapeutic agents effective as anti-tumour agents in the treatment of pancreatic cancer. Such an anti-tumour agent may be a chemotherapeutic agent selected from Gemcitabine, Fluorouracil (5-FU), Capecitabine, FOLFIRINOX (Leucovorin Calcium, Fluorouracil, Irinotecan Hydrochloride and Oxaliplatin), Nab-paclitaxel (Abraxane®) and combinations thereof. An immuno-oncology agent (e.g. a PD-1 inhibitor and/or a PD-L1 inhibitor) may also favourably be used with the CCR1 antagonist.

7 Claims, 30 Drawing Sheets

TCGA Pancreatic adenocarcinoma (PAAD) Samples

A

Experimental Plan : KPC band A mice (tumours < 3mm) will be enrolled and challenged in a randomised, 5-arm intervention study 1) Cohort 1 (8 mice): Saline : i.p./2x week + cyclodextrin p.o./daily + Saline i.p./days 4, 7 and 10 post-enrolment
2) Cohort 2 (8 mice): Gemcitabine ; 100mg/kg; i.p./2x week (every Tues/Fri for study duration)
3) Cohort 3 (8 mice): BX471 ; 30 mg/kg; p.o./daily (for study duration)
4) Cohort 4 (8 mice): Gemcitabine ; 100mg/kg; i.p./2x week + BX471 ; 30 mg/kg; p.o./daily (for study duration)
5) Cohort 5 (8 mice): Gemcitabine ; 100mg/kg; i.p./2x week + BX471 ; 30 mg/kg; p.o./daily + anti-PD-1; 200ug/dose; i.p./day 4, 7 and 10 post-enrolment

B

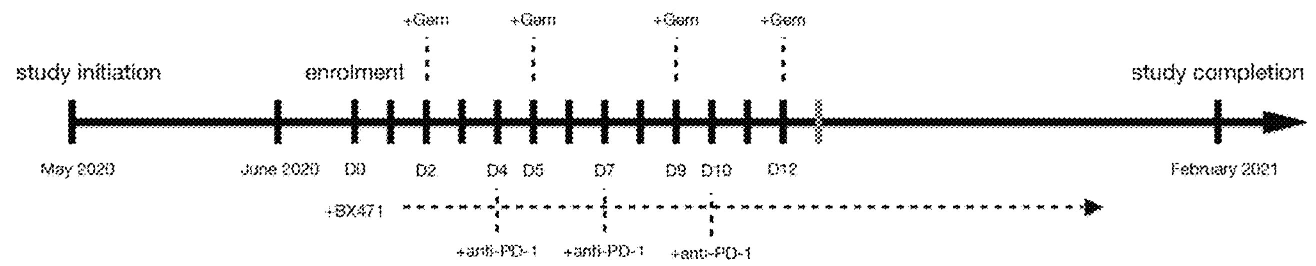

FIGURE 25

TREATMENT AND PROGNOSIS OF PANCREATIC CANCER

CROSS-REFERENCE TO RELATED APPLICATIONS

This application is the National Stage entry under 35 U.S.C. § 371 of International Application No. PCT/GB2020/053295, filed on Dec. 18, 2020, published on Jun. 24, 2021 under Publication Number WO 2021/123813 A8, the entirety of which is herein incorporated by reference.

INTRODUCTION

The present invention relates to the use of CCR1 antagonists in the treatment of pancreatic cancer. The present invention also relates to the use of pharmaceutical compositions comprising CCR1 antagonists, and to use of CCR1 antagonists in combination with one or more other therapeutic agents for the treatment of pancreatic cancer. Novel methods of treatment and prognosis for pancreatic cancer are also described.

BACKGROUND OF THE INVENTION

Pancreatic cancer is an aggressive form of cancer which displays very few symptoms until the cancer is in an advanced state. As the name suggests, pancreatic cancer is a disease in which malignant (cancerous) cells form in the tissue of the pancreas. Pancreatic cancer currently represents the tenth most common form of cancer diagnosed in the UK, with 9,912 cases of pancreatic cancer diagnosed in the UK in 2015. Survival rates for patients diagnosed with pancreatic cancer are strikingly low, with is less than 1% of patients diagnosed with pancreatic cancer surviving for more than 10 years. In 2016 alone, 9,263 people in the UK died from pancreatic cancer, a number which roughly correlates to the number of people diagnosed with pancreatic cancer in the UK in the same year.

While significant improvements in prevention, detection and treatment over the last 40 years have revolutionised the survival rates of patients diagnosed with most other forms of cancer, clinical outcome for patients diagnosed with pancreatic cancer have remained unyieldingly poor. Pancreatic ductal adenocarcinoma (PDAC), which constitutes over 90% of all pancreatic cancer cases, sees roughly 140,000 new cases globally, making it the fourth-leading cause of cancer-related deaths in the world.

The poor clinical outcomes and low survival rates associated with pancreatic cancer are, in part, due to the lack of effective treatment options that are currently available for treating the disease. For instance, the current first-line options for unresectable pancreatic cancer, gemcitabine (Gemzar®) plus nab-paclitaxel (Abraxane®)) and/or FOLFIRINOX (a combination of fluorouracil, leucovorin, irinotecan and oxaliplatin), are chemotherapeutic agents which, if administered to an individual diagnosed with unresectable pancreatic cancer, will on average only extend the life of the individual by 11 months.

There, therefore, remains a need for new and improved treatments regimens for pancreatic cancer. Also desired are new methods for prognosing and stratifying patients who have been diagnosed with the disease, such that medical practitioners can make more informed decisions on how best to treat patients with advanced forms of pancreatic cancer.

SUMMARY OF THE INVENTION

According to a first aspect of the present invention, there is provided a CCR1 antagonist, a pharmaceutically acceptable salt, solvate or hydrate thereof, for use in the treatment of pancreatic cancer.

The present inventors determined there to be a strong correlation between CCR1 expressed in pancreatic cancer cells (e.g. PDAC cells) and patient prognosis; the inventors found that high levels of CCR1 correlated strongly to patients with the worst clinical outcomes. The inventors further found that high levels of immune (e.g. macrophage) infiltration also correlated well with poor patient prognosis. The inventors were therefore able to identify new biomarkers and methods for prognosing pancreatic cancer patients.

Furthermore, the inventors found that a number of structurally distinct CCR1 antagonists were effective at both disrupting macrophage-mediated pro-invasive characteristics of pancreatic cancer cells, and reducing CCR1 expression levels. In vivo tumour growth studies confirmed that the administration of a CCR1 antagonist (e.g. BX-471) resulted in a significant inhibition to the growth of pancreatic cancer cells (e.g. PDAC cells), particularly when the pancreatic cancer cells were also exposed to macrophages. The inventors have also found that inclusion of a CCR1 antagonist with standard of care drug treatment increased the survival time of mice in a murine model of pancreatic ductal adenocarcinoma (PDAC).

A CCR1 antagonist for use according to the invention is especially effective in the treatment of pancreatic cancer when it is used in combination with an established treatment regimen, such as a treatment often referred to as 'standard of care'. Such combinations are discussed in further detail below. In a preferred embodiment, there is provided a CCR1 antagonist, or a pharmaceutically acceptable salt, solvate or hydrate thereof, for use in the treatment of pancreatic cancer in combination with one or more chemotherapeutic agent(s) selected from Gemcitabine (Gemzar®), Fluorouracil (5-FU), Capecitabine (Xeloda®), FOLFIRINOX and Nab-paclitaxel (Abraxane®).

The CCR1 antagonist may further, or alternatively be used in combination with an immuno-oncology agent (e.g. PD-1 and/or a PD-L1 inhibitor).

The CCR1 antagonist may further, or alternatively be used in combination with an MEK inhibitor.

The CCR1 antagonist may further, or alternatively be used in combination with an IGF1R inhibitor.

As mentioned above, the present inventors have found a strong correlation between the level of CCR1 expressed in pancreatic cancer cells (e.g. PDAC cells) and patient prognosis. The treatment of the present invention is thus, in one embodiment, the treatment of a subject who has been identified as having increased levels of CCR1 expression compared to a reference expression level.

As mentioned above, the present inventors have found a strong correlation between the level of immune (e.g. macrophage) infiltration and patient prognosis. The treatment of the present invention is thus, in one embodiment, the treatment of a subject in whom increased levels of immune (e.g. macrophage) infiltration have been identified compared to a reference infiltration level. In some embodiments, the macrophages are M1 macrophages. In other embodiments, the macrophages are M2 macrophages. That is to say, suitably, the macrophage infiltration referred to herein will be understood to be M1 or M2 macrophage infiltration.

Suitably, the CCR1 antagonist in respect of any aspect of the present invention is selected from UCB-35625, BX-471, AZD-4818, and J113863, or a pharmaceutically acceptable salt, solvate or hydrate thereof.

DETAILED DESCRIPTION OF THE INVENTION

no differential overall survival calculated in pancreatic cancer patients according to immune infiltration status (immune score), however; higher overall survival calculated in pancreatic cancer patients with low levels of M1 or M2-like macrophage signature (p=0.01). *Low<30 percentile<Medium<70 percentile<High.

Figure 3:
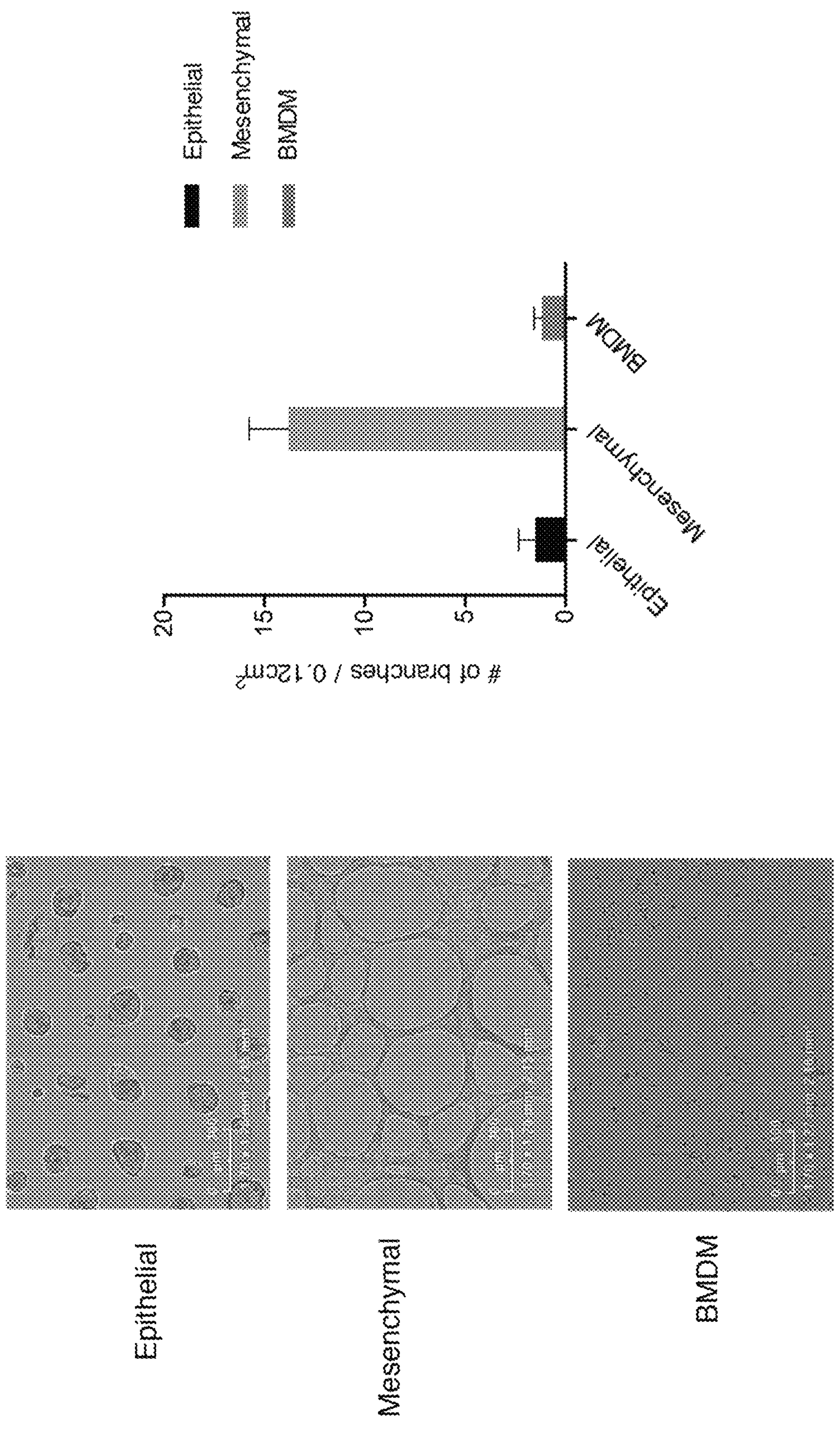

FIG. 3 shows the murine PDAC mesenchymal cells form vascular mimicry in a 3D in vitro assay of invasion. PDAC mesenchymal cells form vascular mimicry (VM)-like structures when grown on plates pre-coated with 100% matrigel, in contrast to PDAC epithelial cells, which form cell clusters. Quantification of vascular structures taken at 96 hours post-seeding (p=0.01).

Figure 4:
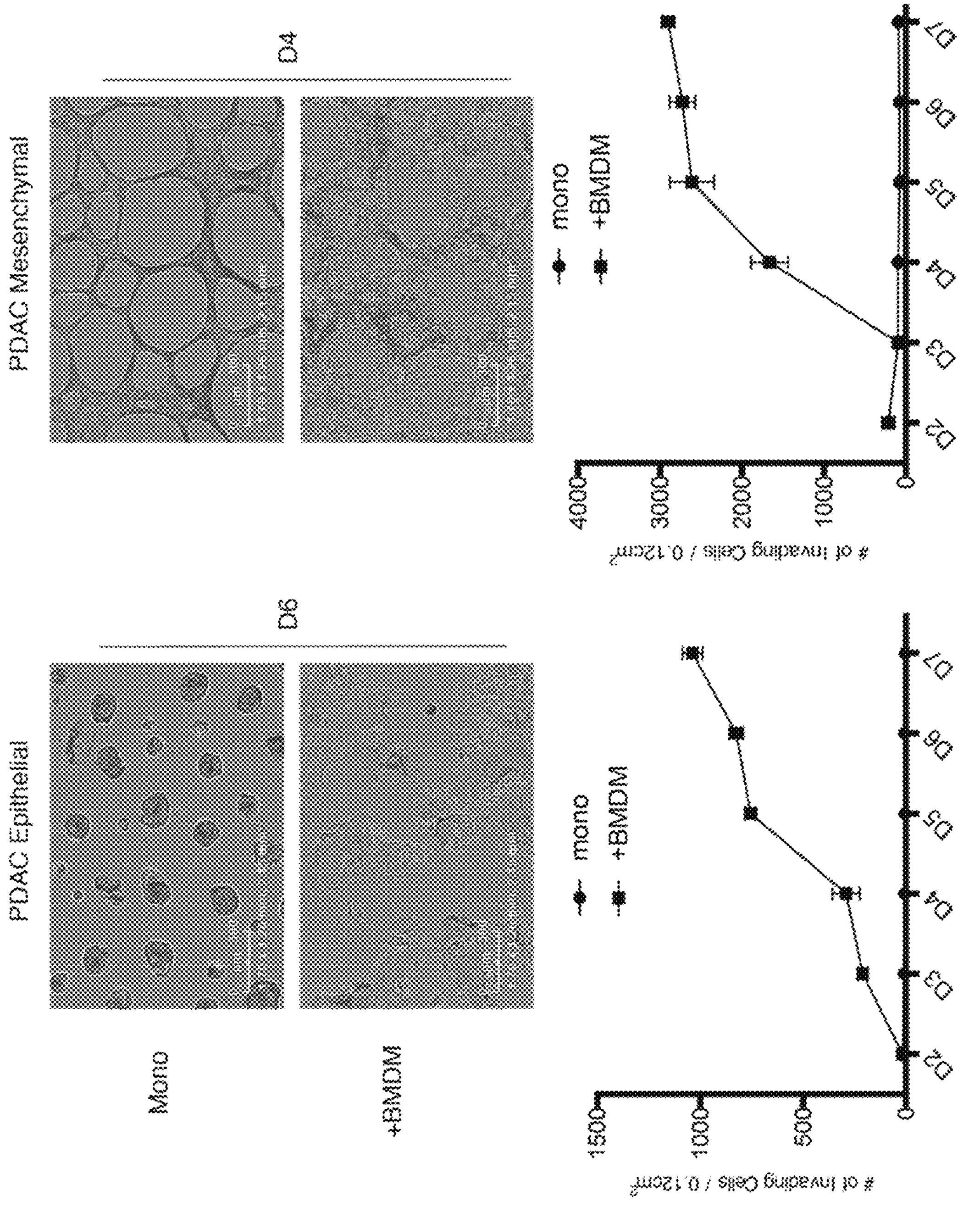

FIG. 4 shows mCherry-labelled PDAC epithelial and mesenchymal cells with ZsGreen-labelled primary bone marrow-derived macrophages (BMDM) in 3D cell culture imaged by IncuCyte Zoom over 7 days. Representative images and quantification of pro-invasive phenotype taken at day 6 and day 4 for PDAC epithelial and PDAC mesenchymal, respectively. Scale bar, 300 microns.

Figure 5:
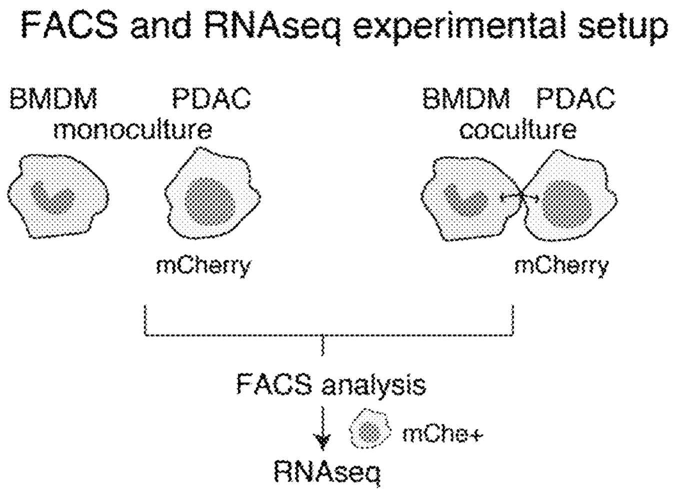
Figure 5:
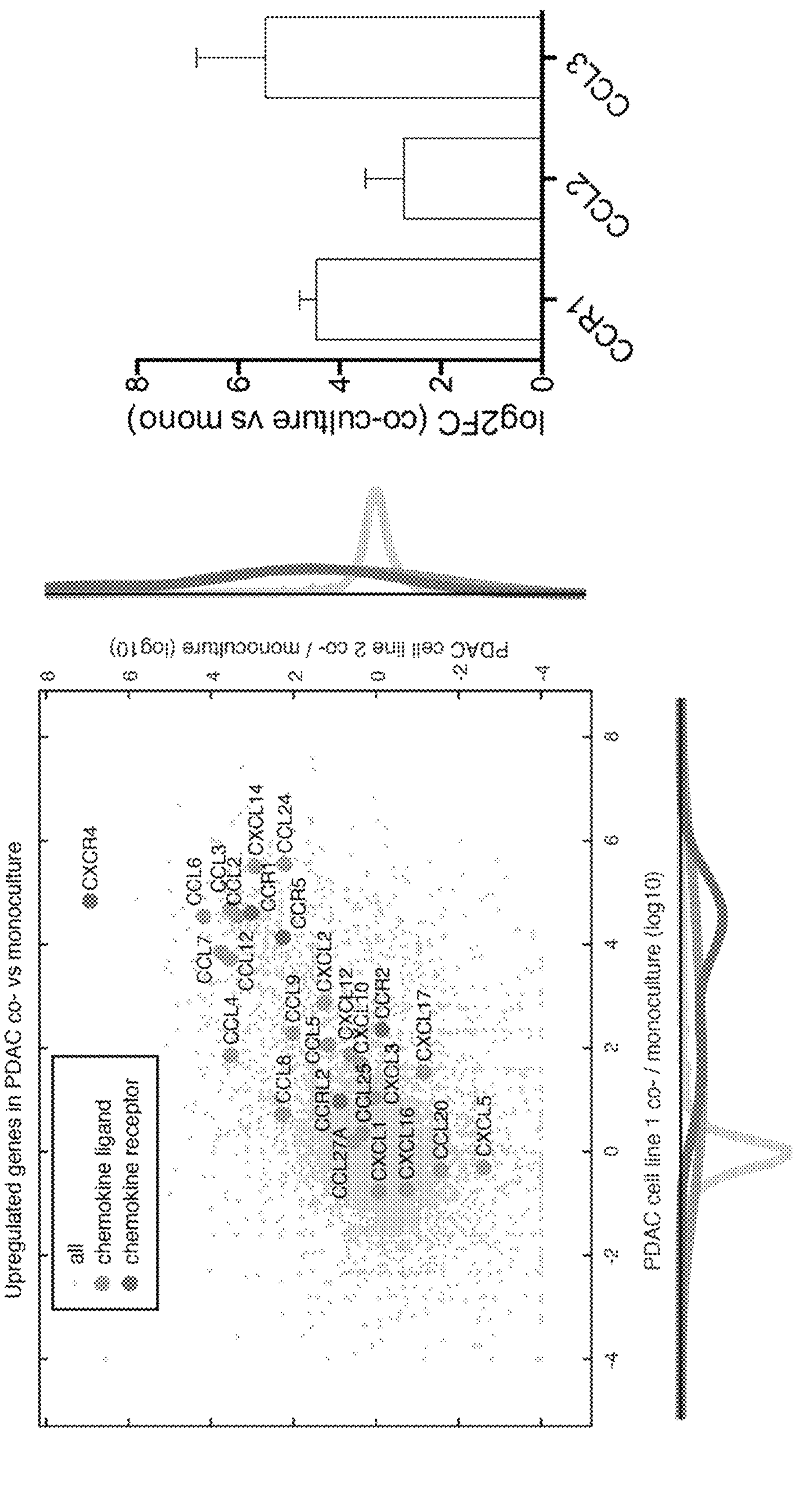

FIG. 5 shows: A) a schematic of mono-culture or admixed PDAC and BMDM cells in in 2D culture with subsequent fluorescence-activated cell sorting (FACS) for downstream RNA-sequencing analysis; B) Chemokines and their receptors are amongst highest differentially expressed genes in PDAC transcriptomes following prolonged co-culture with BMDM; and C) Confirmation of RNA-sequencing data by qRT-PCR in PDAC cells following prolonged co-culture with BMDM.

Figure 6:
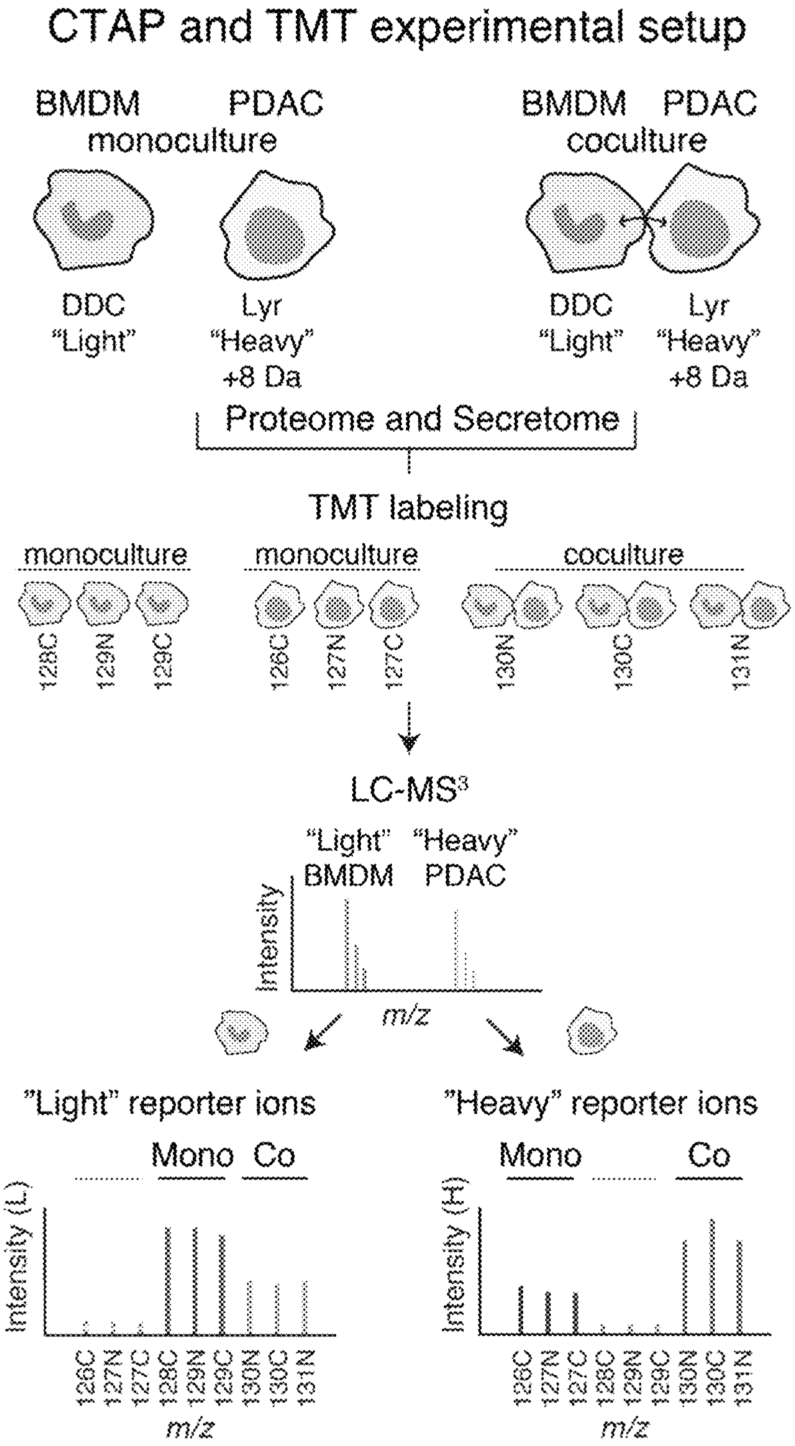

FIG. 6 shows a schematic of mono-culture or admixed PDAC and BMDM cells in in 2D culture CTAP (cell-type specific labelling using amino acid precursors)-labelled to identify novel protein targets (proteome) that promote PDAC cell invasion. Mono-cultures and mixed co-cultures were harvested in bulk for downstream proteome and secretome analysis.

Figure 7:
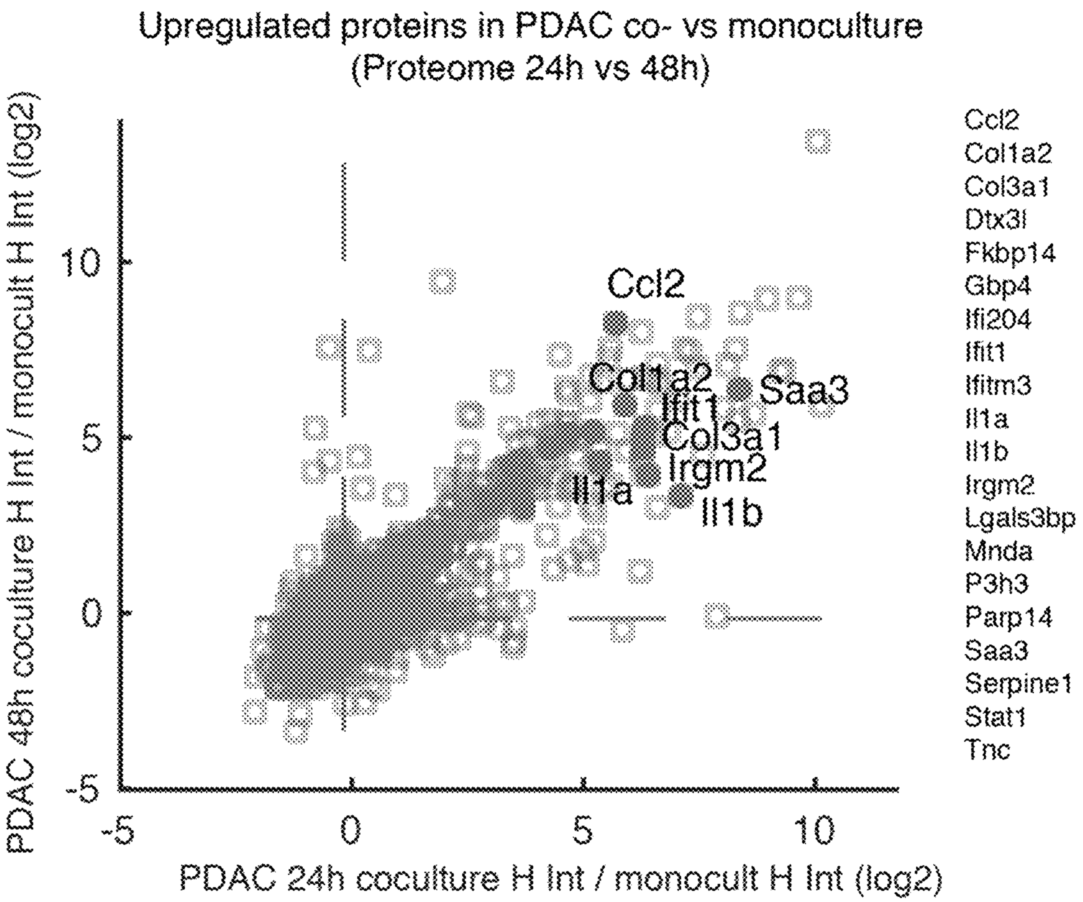

FIG. 7 shows the results of the proteomic approach of FIG. 6. CTAP-TMT (tandem mass tag) proteome reveal chemokines and their receptors as amongst highest differentially expressed genes in PDAC following prolonged co-culture with BMDM.

Figure 8:
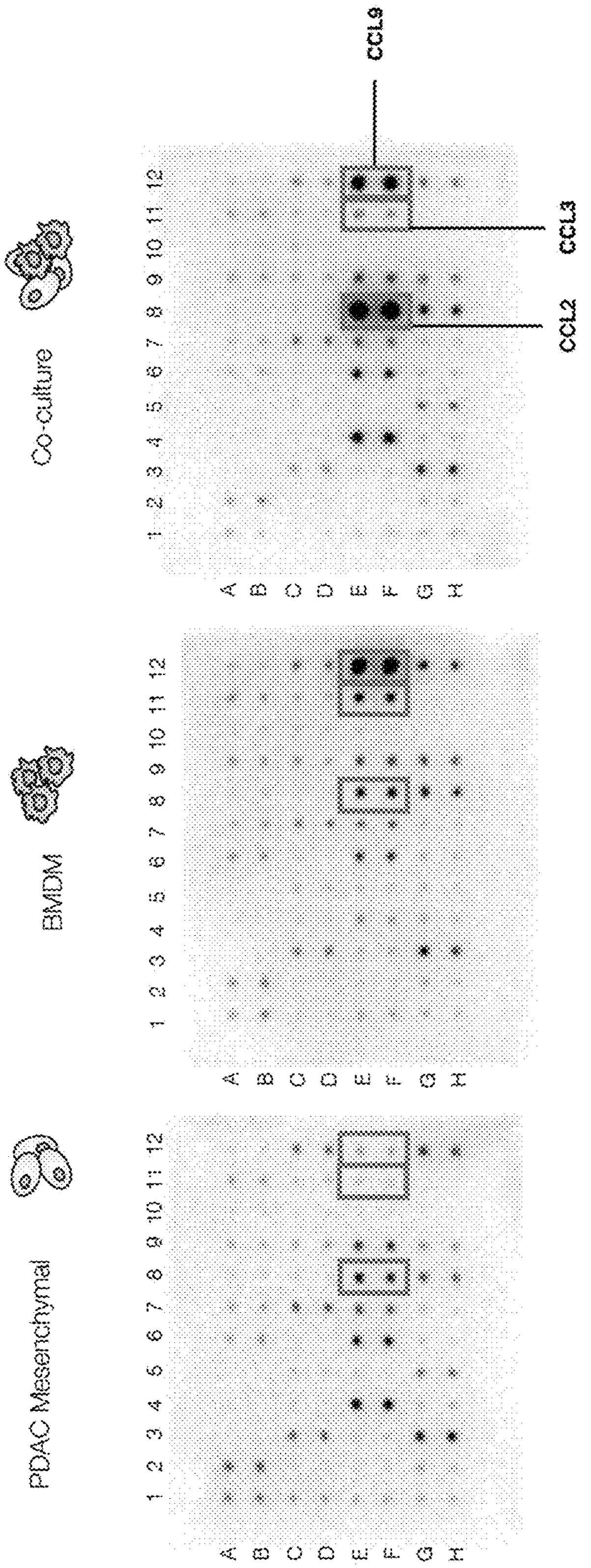

FIG. 8 shows the results of secretome approach of FIG. 6. Shown are representative inflammation antibody arrays probed with conditioned media (CM); PDAC and BMDM cells in mono-culture or admixed together in 2D culture.

Figure 9:
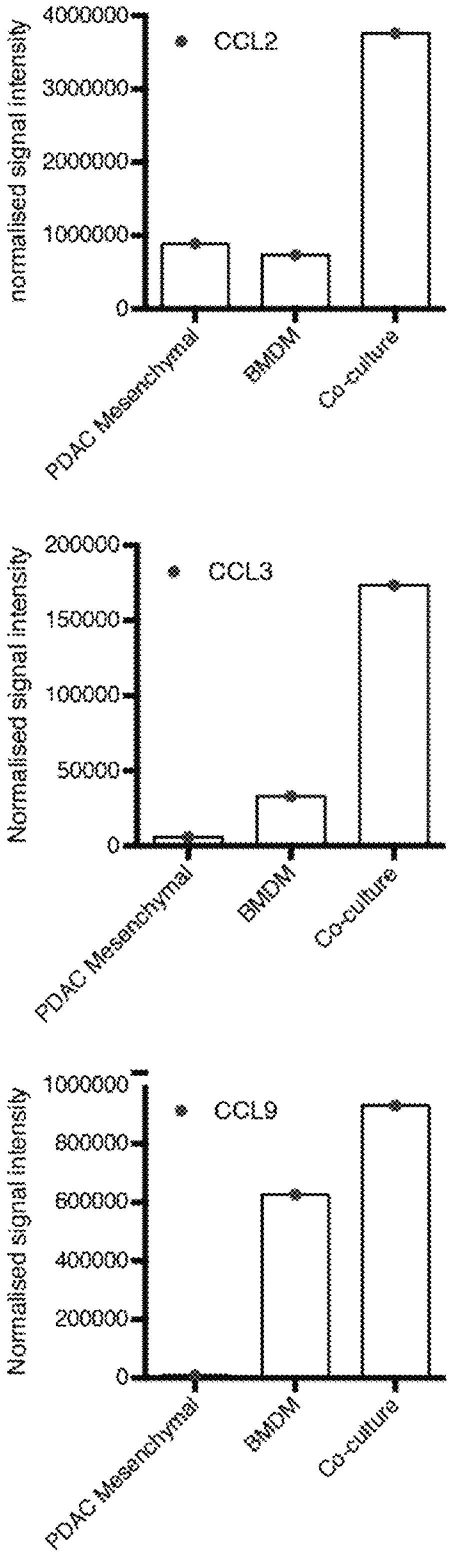

FIG. 9 shows the quantification of the various CCL chemokines derived from arrays shown in FIG. 8.

Figure 10:
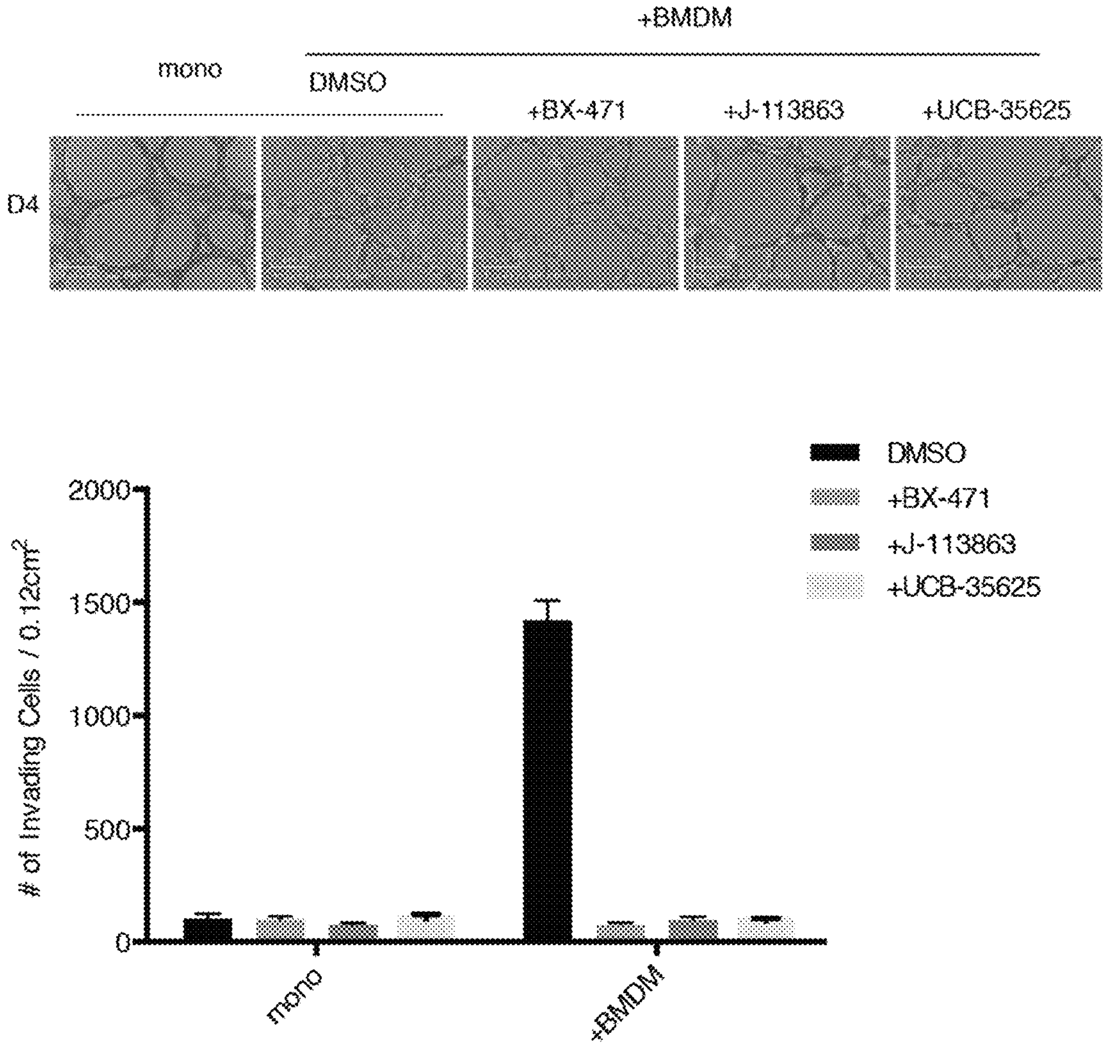

FIG. 10 shows mCherry-labelled PDAC mesenchymal cells with ZsGreen-labelled BMDM in 3D cell culture, treated with various small molecule inhibitors of CCR1, imaged by IncuCyte Zoom over 7 days. Representative images and quantification of pro-invasive phenotype taken at day 4. Scale bar, 300 microns. Below is quantification of pro-invasive phenotype taken at day 4.

Figure 11:
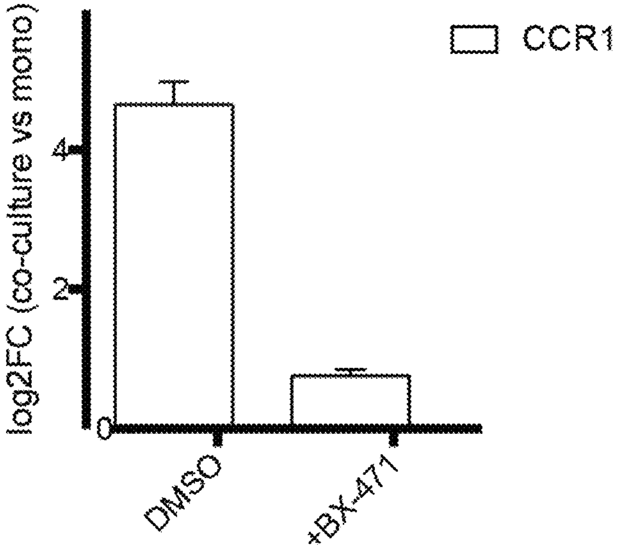

FIG. 11 shows relative CCR1 expression (mRNA) in PDAC mesenchymal cells following co-culture with BMDM in the presence and absence of various CCR1 antagonists by qRT-PCR, matching the data obtained in FIG. 10.

Figure 12:
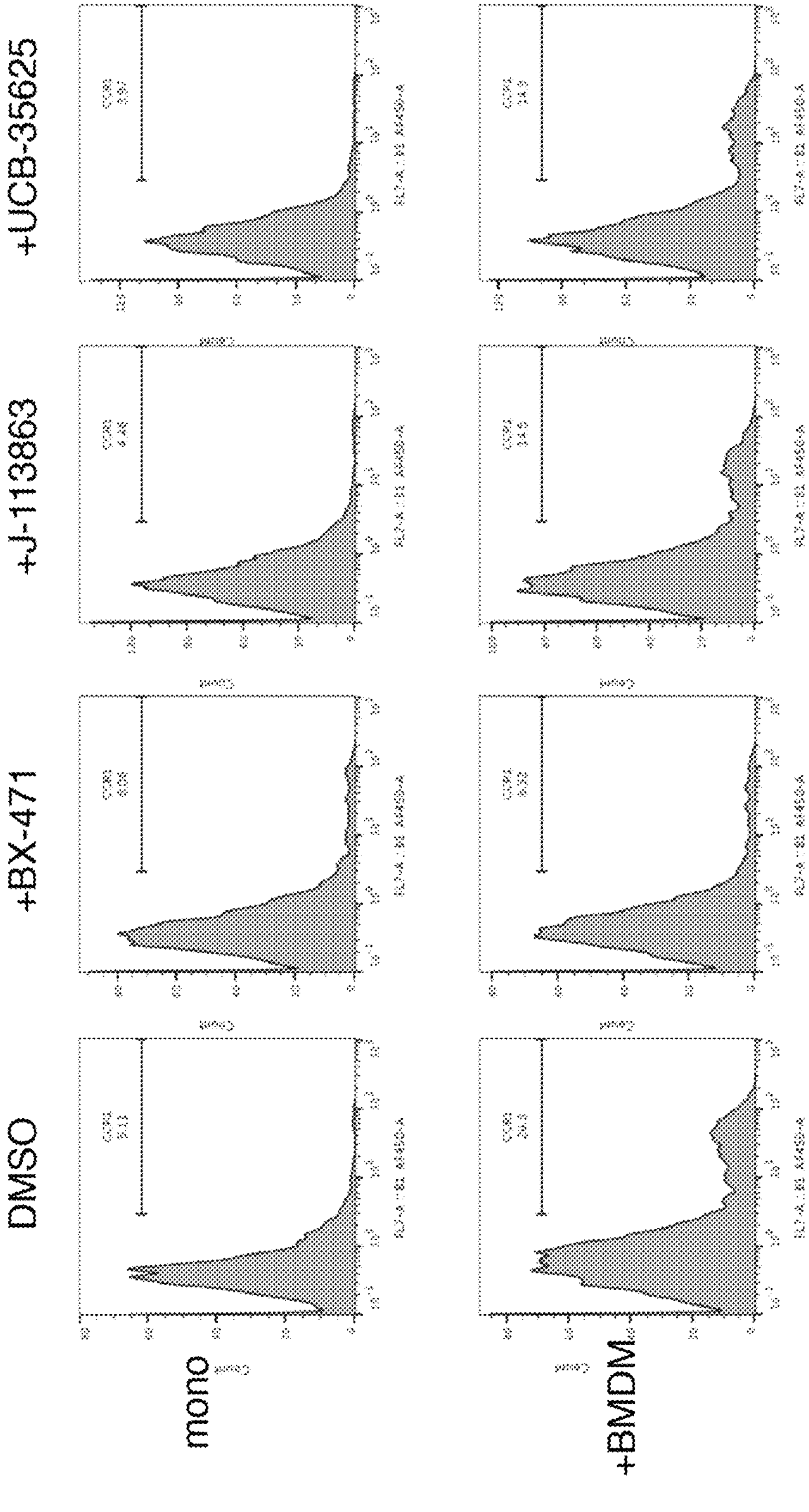

FIG. 12 shows CCR1 expression (protein) in PDAC cells following prolonged co-culture in the presence and absence of various CCR1 antagonists.

Figure 13:
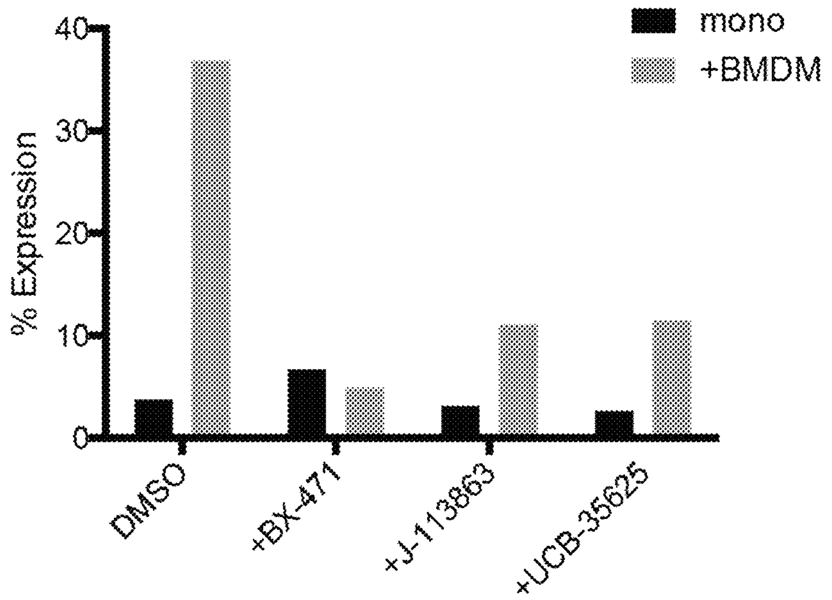

FIG. 13 shows the quantification of CCR1 expression (protein) data shown in FIG. 12.

Figure 14:
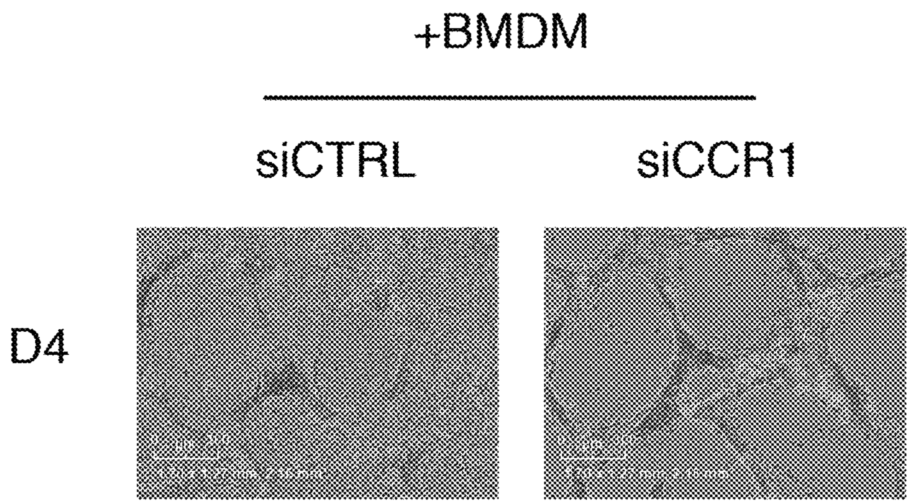

FIG. 14 shows knockdown of CCR1 by siRNA prior to the co-culture of mCherry-labelled PDAC mesenchymal cells with ZsGreen-labelled BMDM in 3D cell culture imaged by IncuCyte Zoom over 7 days. Representative images of pro-invasive phenotype taken at day 4.

Figure 15:
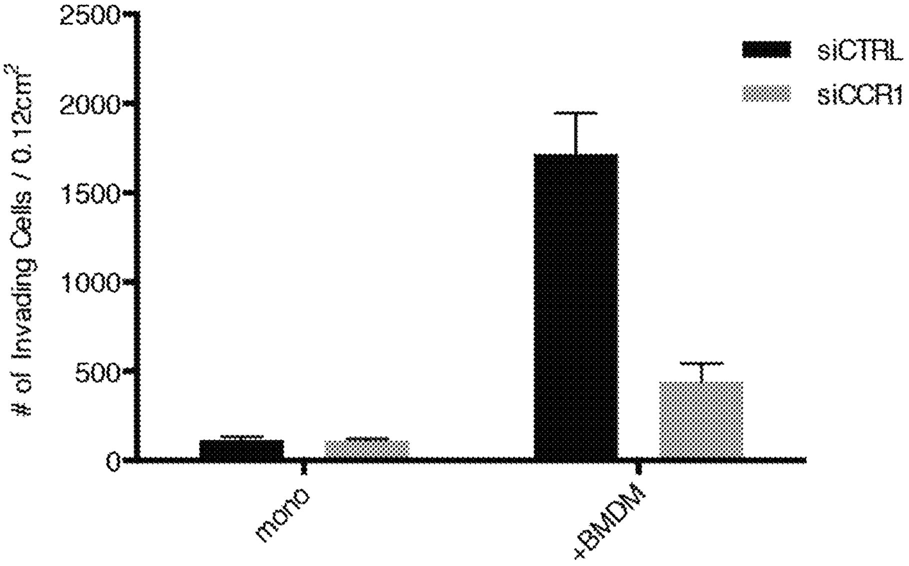

FIG. 15 shows the quantification of the 3D cell culture images of FIG. 14.

Figure 16:
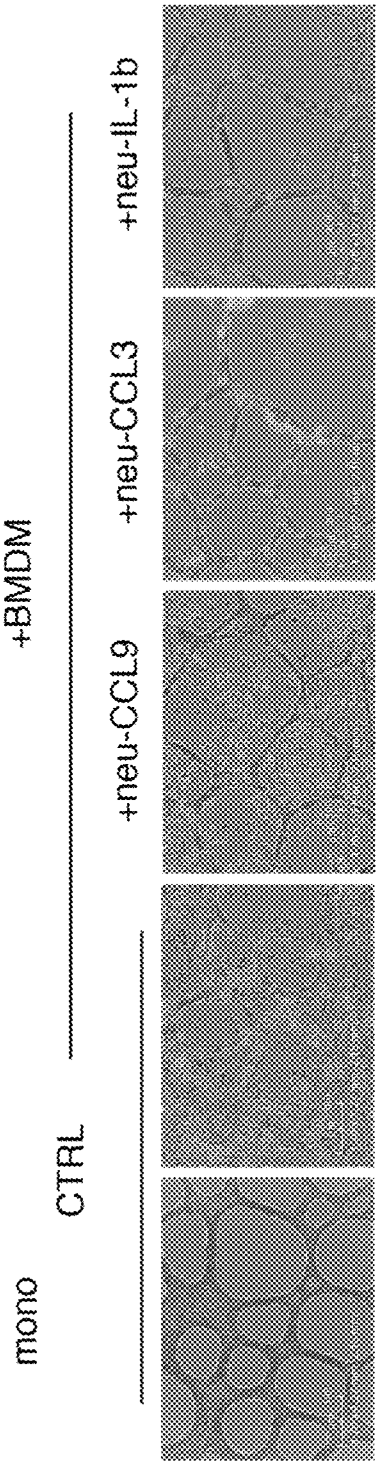
Figure 16:
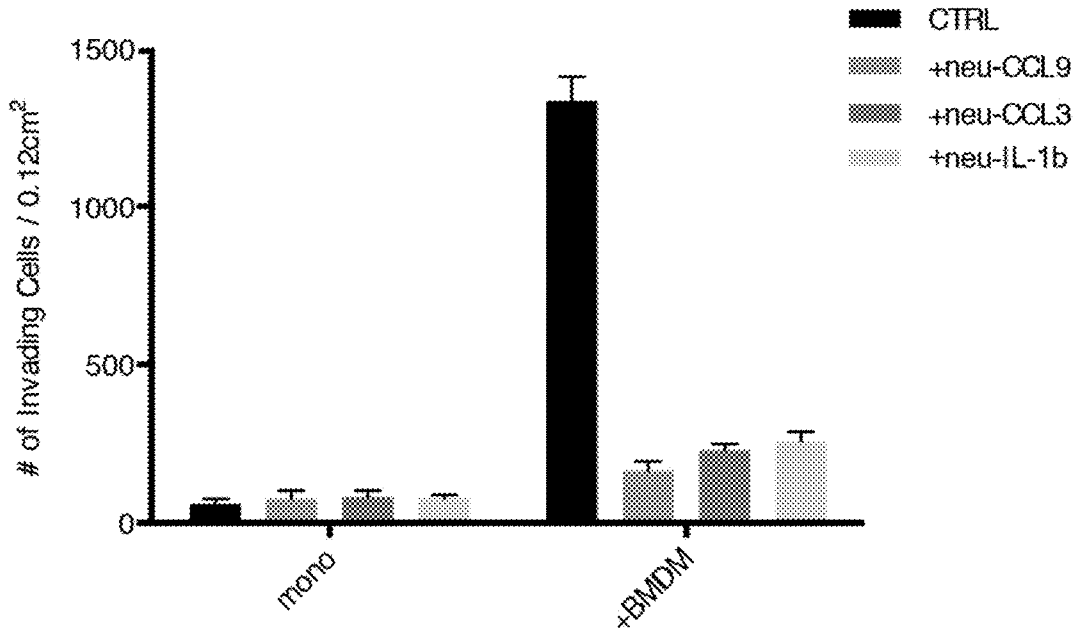

FIG. 16 shows mCherry-labelled PDAC mesenchymal cells with ZsGreen-labelled BMDM in 3D cell culture, treated with various neutralising antibodies to known and novel ligands that bind to CCR1, imaged by IncuCyte Zoom over 7 days. Representative images and quantification of pro-invasive phenotype taken at day 4. Scale bar, 300 microns.

Figure 17:
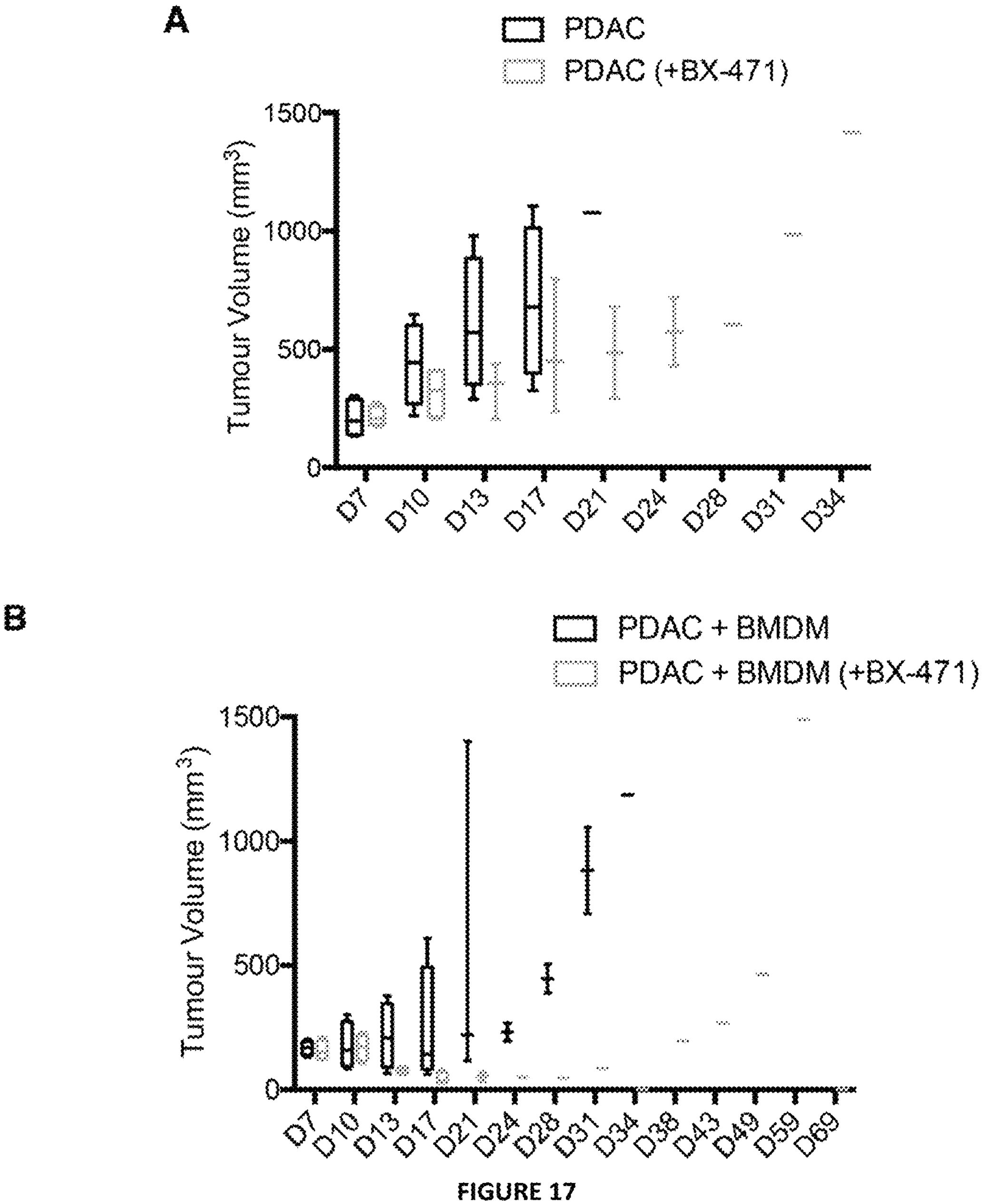

FIG. 17 shows two graphs depicting tumour volume over time (e.g. between 7 and 34 days), for: i) PDAC cells (K84) alone; ii) PDAC cells (K84)+the CCR1 antagonist, BX471; iii) PDAC cells (K84)+bone marrow-derived macrophages; and iv) PDAC cells (K84)+the CCR1 antagonist, BX471+bone marrow-derived macrophages.

Figure 18:
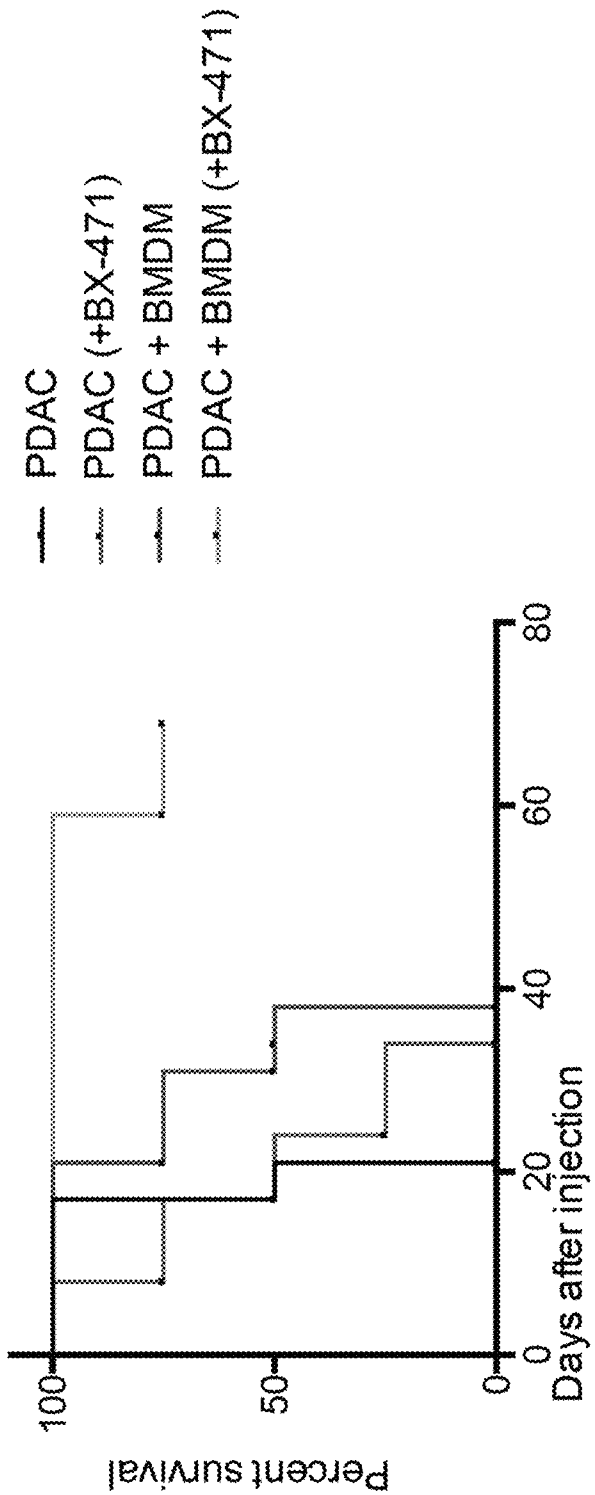

FIG. 18 shows a graph illustrating percentage survival for: i) PDAC cells (K84) alone; ii) PDAC cells (K84)+the CCR1 antagonist, BX471; iii) PDAC cells (K84)+bone marrow-derived macrophages; and iv) PDAC cells (K84)+the CCR1 antagonist, BX471+bone marrow-derived macrophages.

Figure 19:
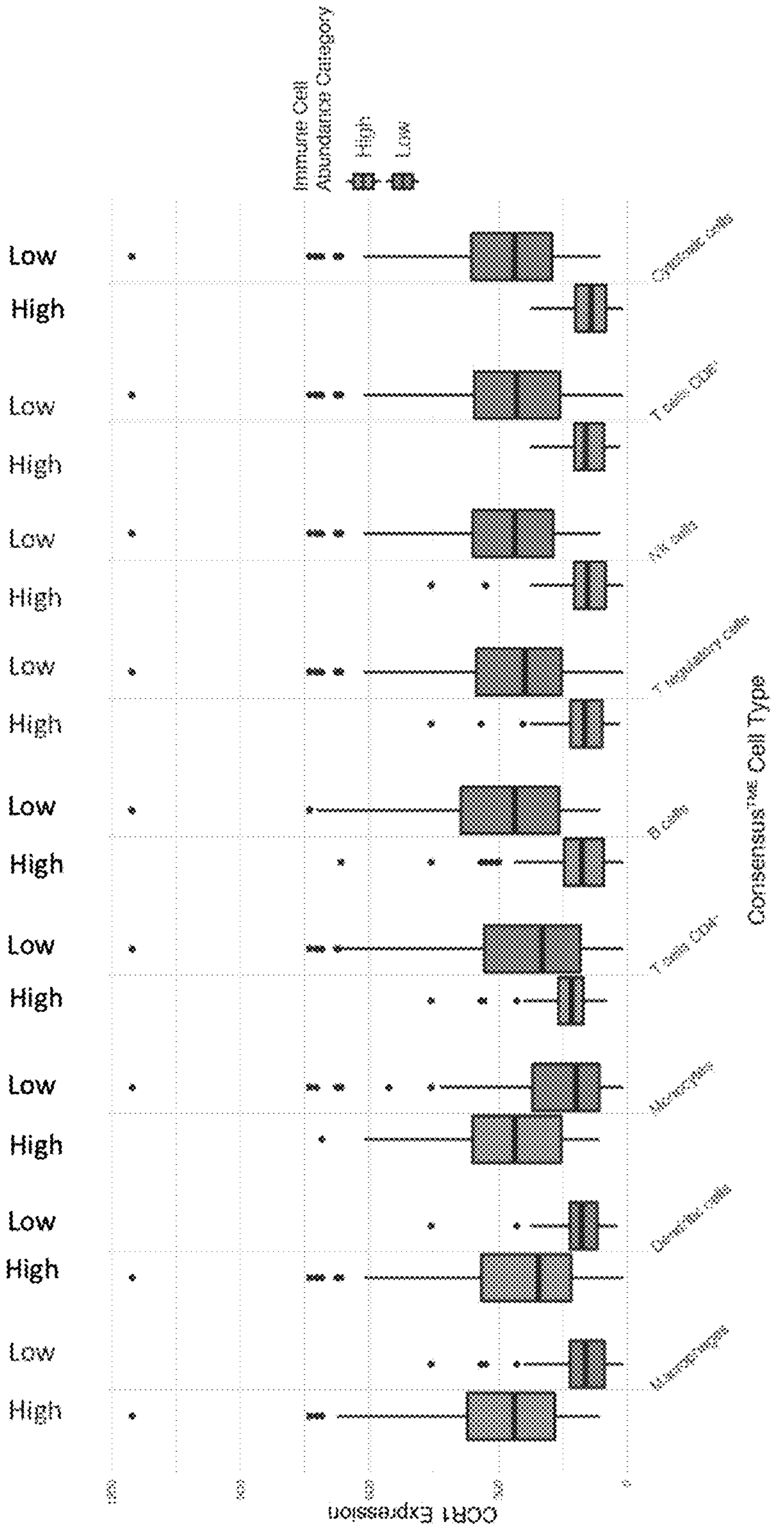

FIG. 19 shows the CCR1 expression of immune cell high/low samples in TOGA pancreatic cancer (PAAD). Each column show bifurcation of samples into high and low for the respective cell type and the CCR1 expression across the group.

Figure 20:
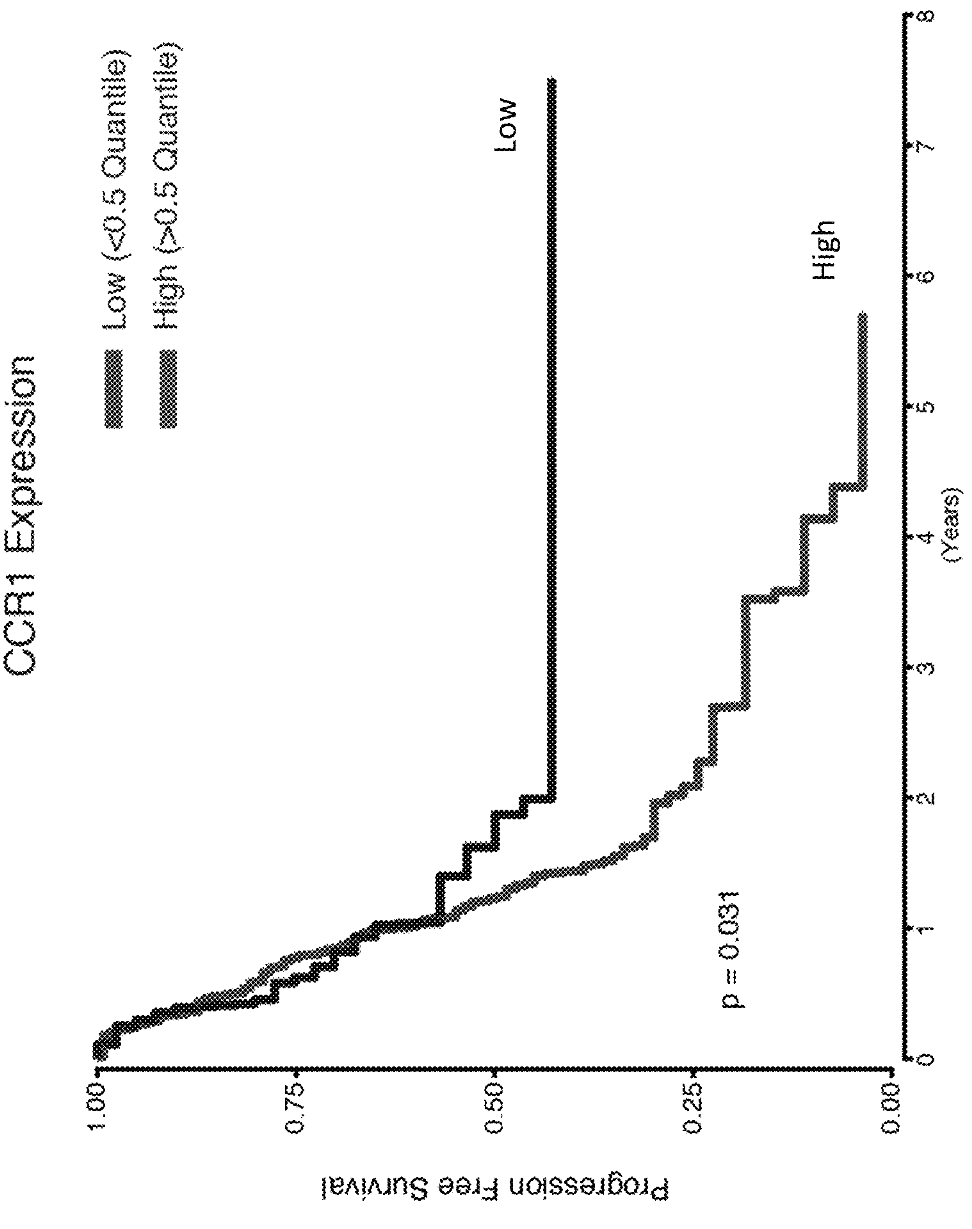

FIG. 20 shows a graph illustrating the survival rate (%) over time generated through Kaplan-Meier Survival Analysis of the data presented in FIG. 19.

Figure 21:
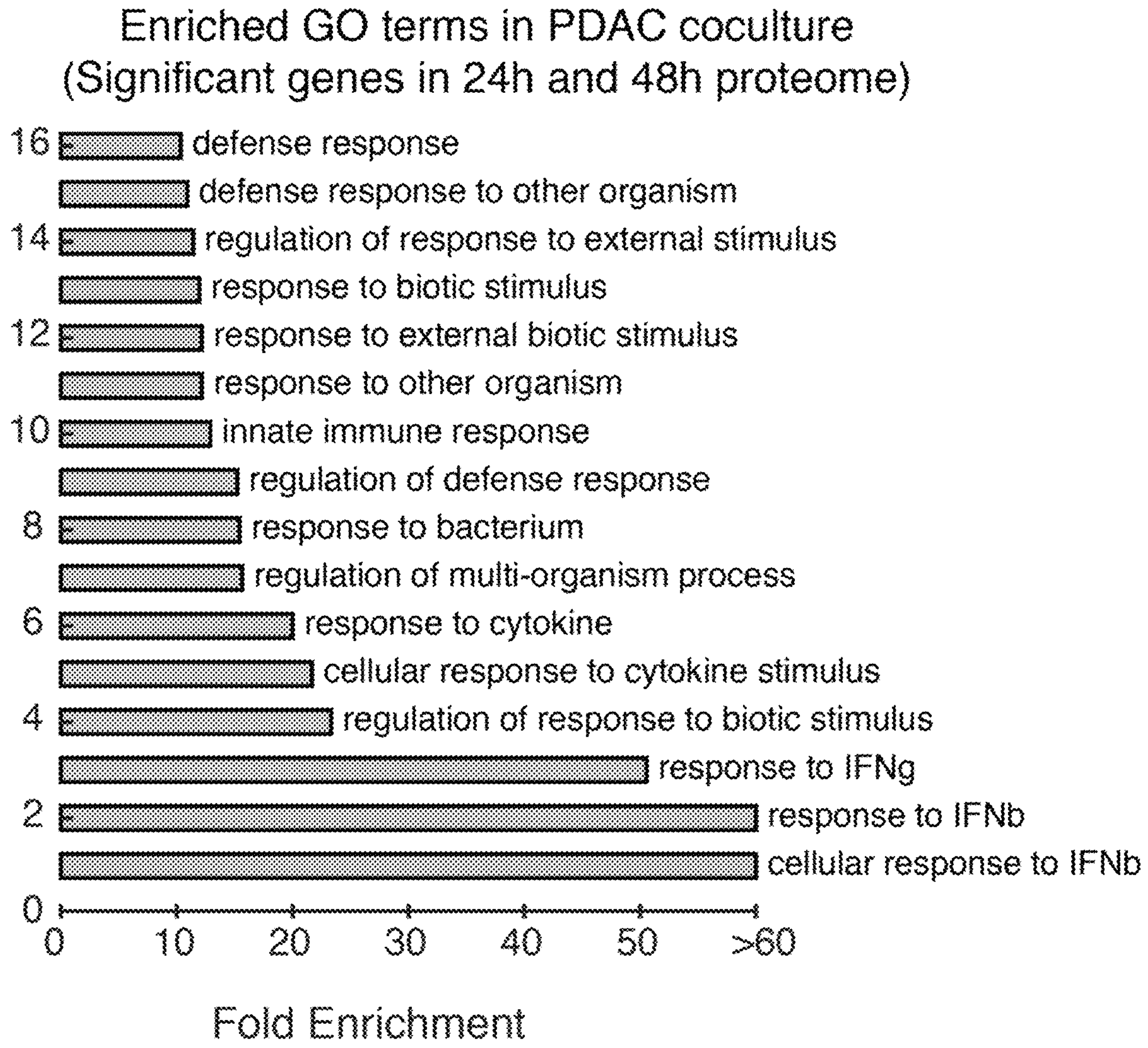

FIG. 21 shows the Gene Ontology (GO) analysis of the most changed proteins following prolonged co-culture reveals enrichment of chemokine related biological processes.

Figure 22:
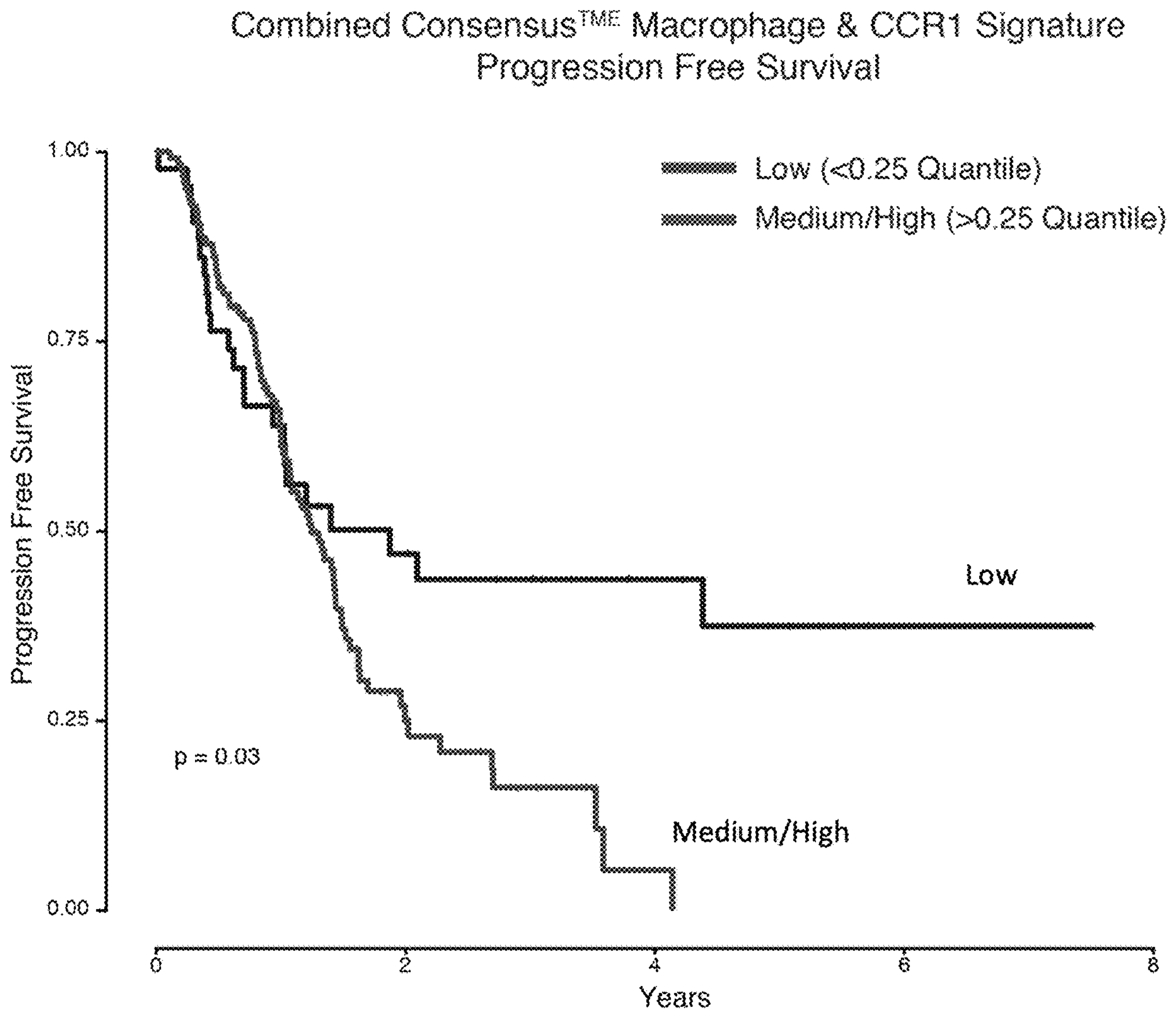

FIG. 22 shows a graph illustrating the survival rate (%) over time generated through Kaplan-Meier Survival Analysis of the combined macrophage infiltration and CCR1 expression data of Example 1.

Figure 23:
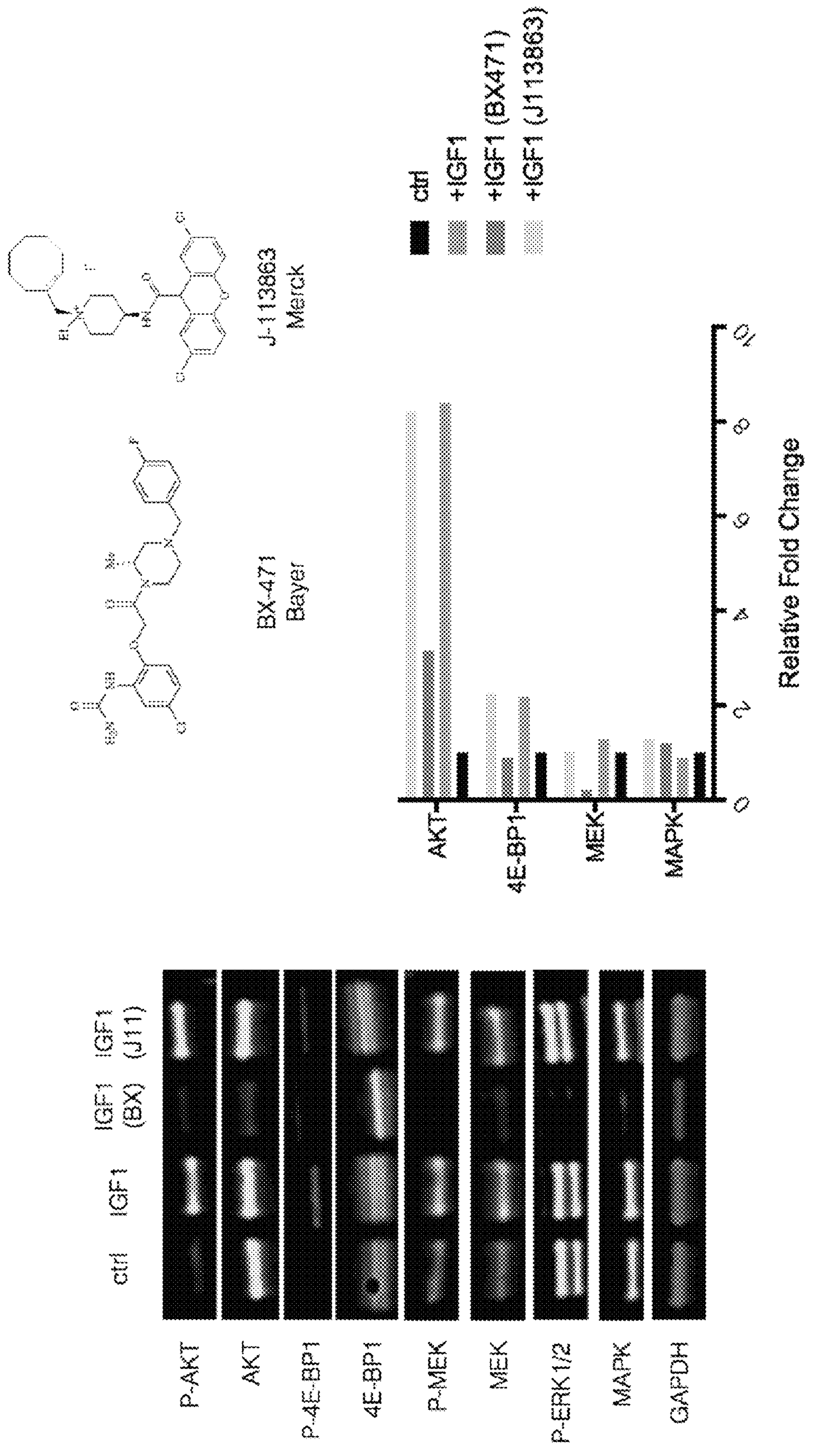

FIG. 23 shows the expression of IGF1 signalling pathway in PDAC mesenchymal cells. Total protein (30 ug) from PDAC cells was resolved by SDS-PAGE gel. Expressions of IGF1 downstream target genes were detected by western blot analysis with anti-AKT, 4E-BP1, MEK and MAPK antibodies. GAPDH was used as a loading control for all samples.

Figure 24:
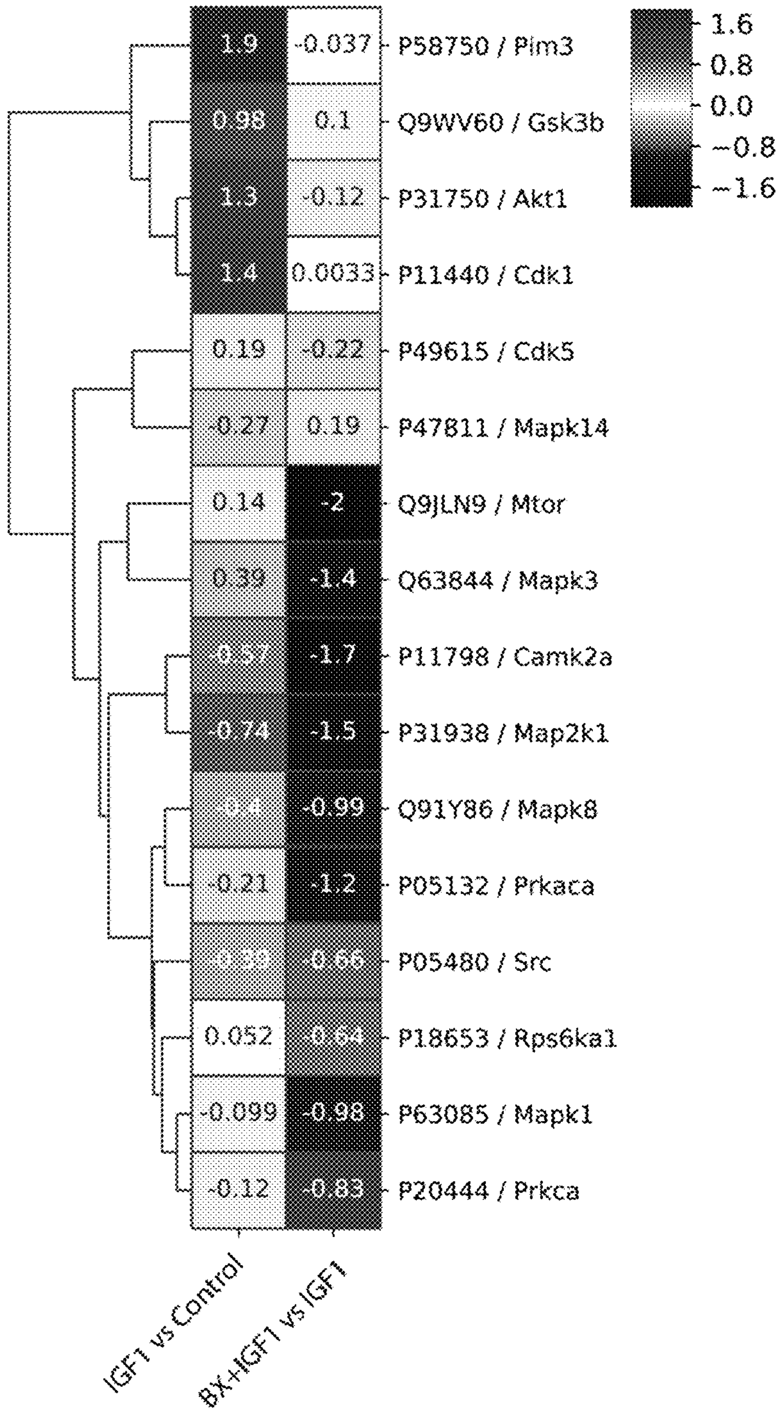

FIG. 24 shows a heatmap plot generated using kinase set enrichment analysis (KSEA) to estimate kinase activity observed for different kinase activity in samples treated with recombinant IGF1 compared to those with a combination of both IGF1 and BX-471.

FIG. 25 shows a study plan to determine the effectiveness of the CCR1 antagonist BX-471 in the treatment of pancreatic cancer, using the KPC mouse model of PDAC. Included are descriptions of the five experimental cohorts used and a timeline showing treatment conditions and study length.

Figure 26:
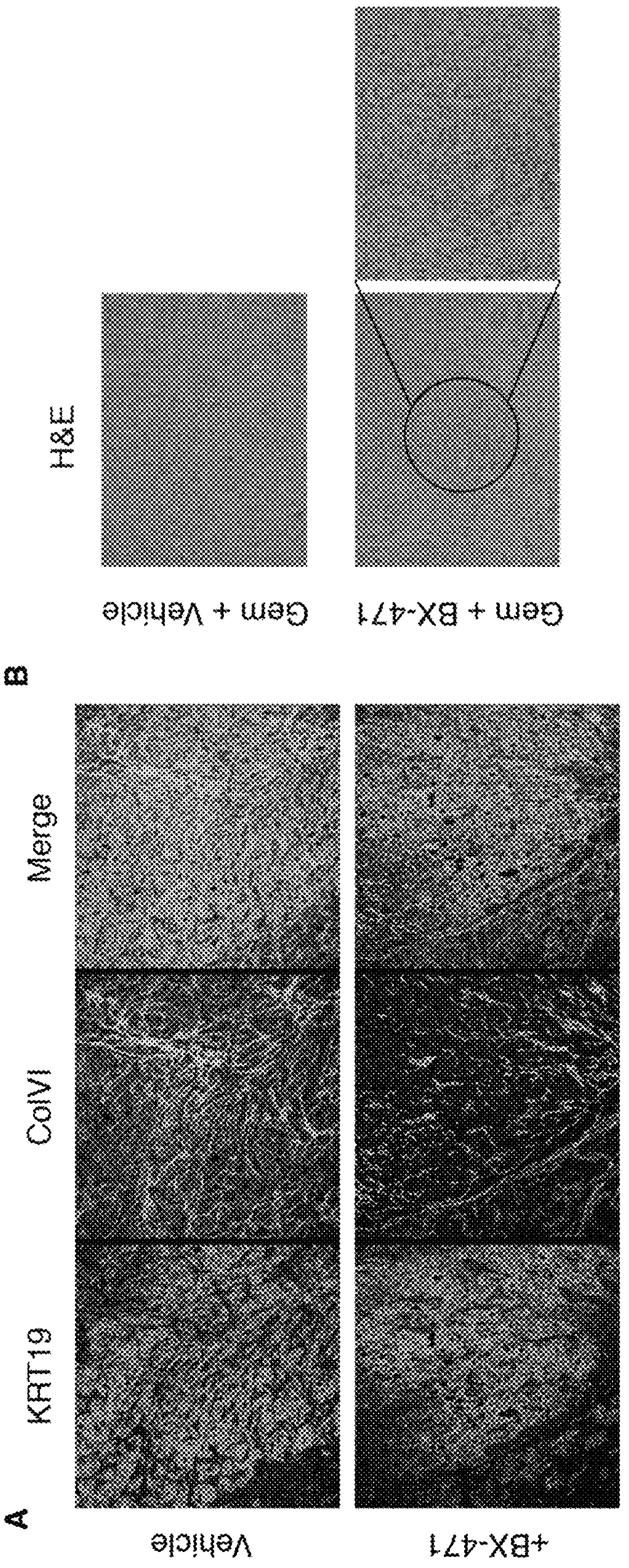
Figure 26:
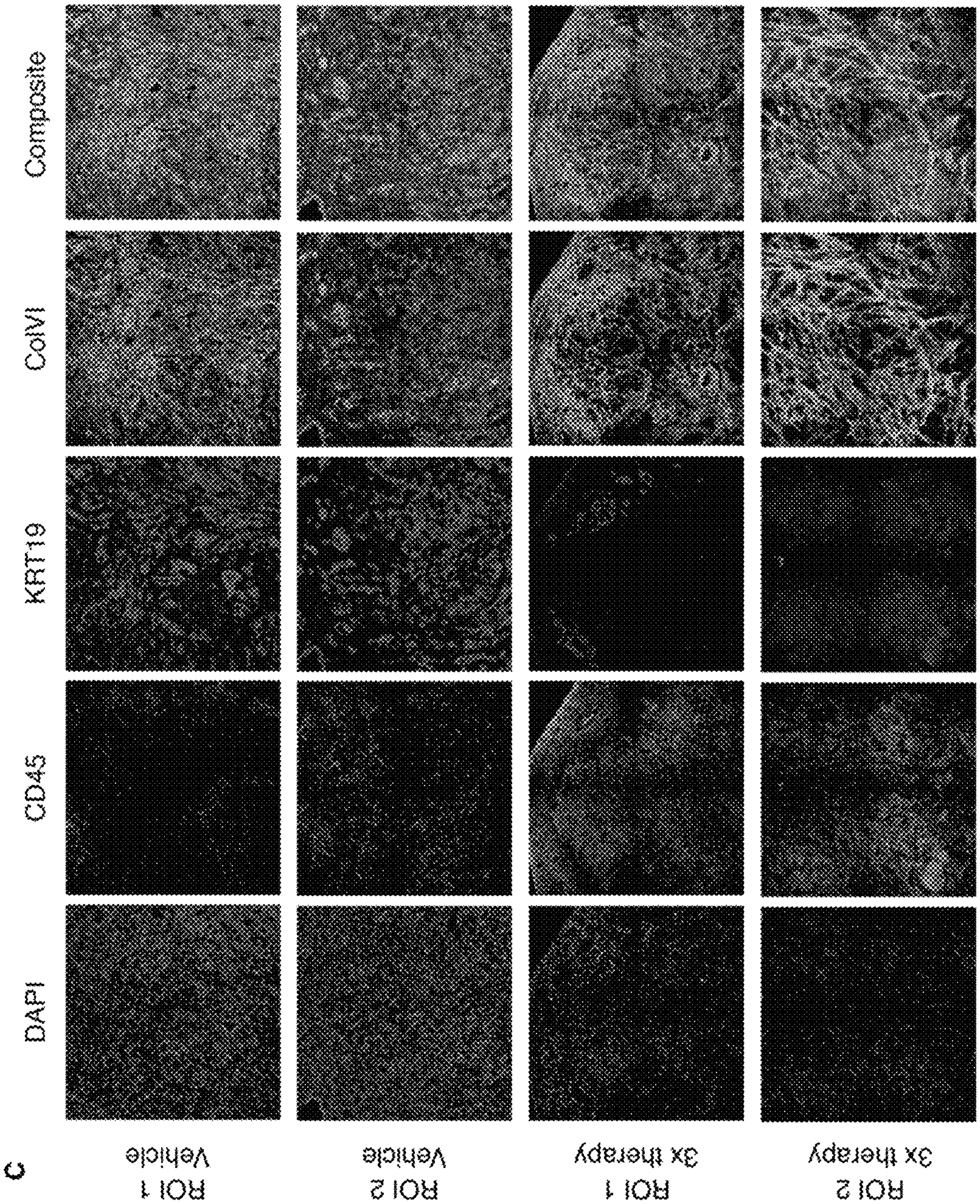

FIG. 26 shows preliminary imaging of primary tumours from KPC mice (treated with either:

vehicle; BX-471; gemcitabine; gemcitabine+BX471; or gemcitabine+anti-PD1+BX-471), stained for collagen IV, immune cells (H&E and CD45), and cancer cells (KRT19).

Figure 27:
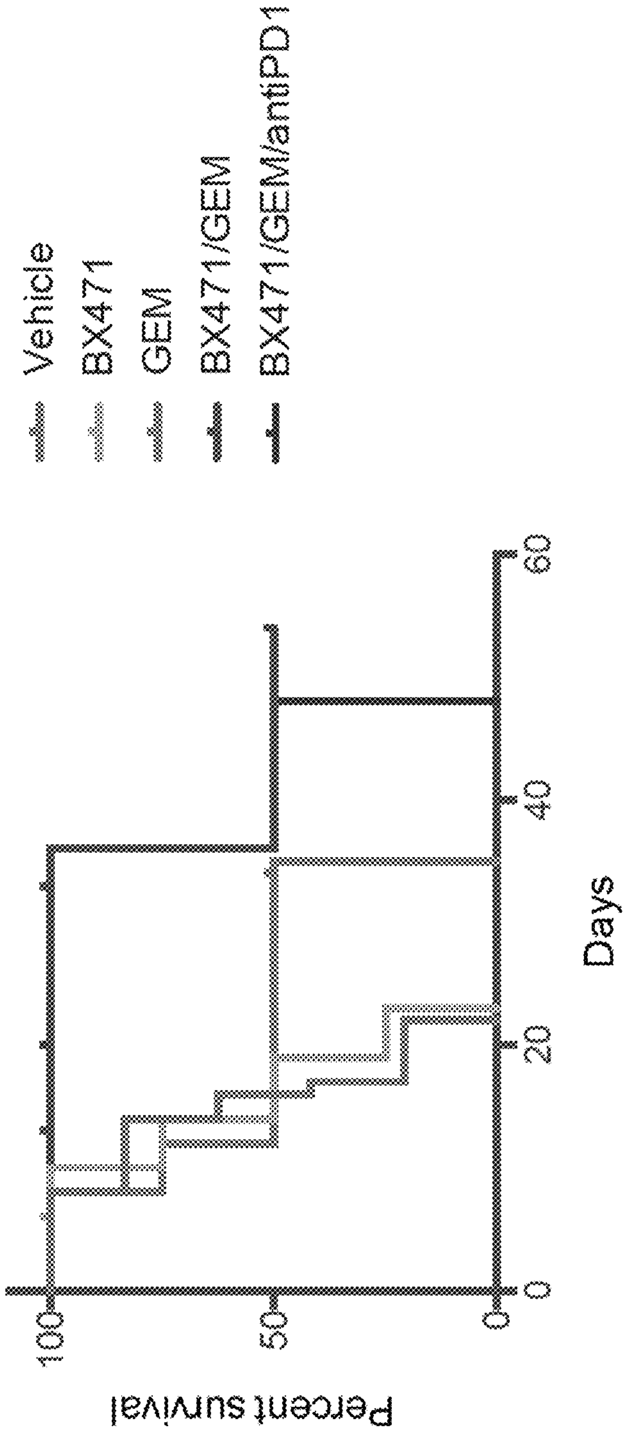

FIG. 27 shows a graph illustrating the survival rate (%) over time for KPC mice treated with: (i) vehicle; (ii) BX-471; (iii) gemcitabine; (iv) gemcitabine+BX471 double therapy; or (v) gemcitabine+anti-PD1+BX-471 triple therapy.

CCR1 ANTAGONISTS

C—C chemokine receptor type 1 (CCR1), a protein encoded by the CCR1 gene, is a member of the beta chemokine receptor family, a family of receptors which are known to play an active role in the mediation of signal transduction and the recruitment of effector immune cells to a site of inflammation. Due to the active involvement of CCR1, and other chemokine family members (e.g. CCR2, CCR3 and CCR5), in mediating an immune response, several small molecule antagonists of CCR1, and CCR1-neutralising antibodies, have been developed and shown to be highly effective in the treatment of autoimmune diseases and chronic inflammatory diseases.

Despite the widespread use of CCR1 antagonists in the treatment of autoimmune diseases and inflammatory disorders, there have been very few reports of CCR1 antagonists being used as effective agents for the treatment of aggressive forms of solid cancers, which are generally considered to be much more challenging to treat than other forms of cancer (as is evidenced by the poor survival rates amongst pancreatic cancer patients).

The US patent application US2017/0290808 reports that specific combinations of certain CCR1 antagonists (e.g. small molecule antagonists of CCR1) and PD-1 and/or PD-L1 inhibitors may be useful in the treatment of breast cancer metastasis, such as, for example, triple negative breast cancer metastasis. However, US2017/0290808 contains no data to support, or give reason to suspect, that CCR1 antagonists could be used to treat more aggressive forms of cancer, such as, for example, pancreatic cancer, nor any data to support the use of CCR1 antagonists in the treatment of primary cancers. Furthermore, as pancreatic cancer cells typically have higher amounts of collagen and/or extracellular matrix (ECM) than many other forms of solid tumours, pancreatic cancer is generally regarded as a structurally distinct form of solid cancer (Weniger et al., Cancers, 2019, 10(9), 316). That is to say, the high levels of collagen and/or ECM that are typically found in pancreatic cancer cells limits the access of chemotherapeutic agents to the pancreatic cancer cells, which in turn means many chemotherapeutic agents cannot be effectively be used in the treatment of pancreatic cancer.

In US2009/0286823, it is reported that certain CCR1 inhibitors are useful for the treatment of multiple myeloma and other disorders. Pancreatic cancer is mentioned in a list of cancers that the authors speculate the inhibitors might be useful for. No data are provided to support any suggestion that the compounds described therein would be effective in the treatment of pancreatic cancer on its own or in combination with any other therapy.

In US2013/0280254, it is reported that antagonism of the CCR1 receptor with certain antagonists can inhibit metastasis of a tumour in a patient. Pancreatic cancer is mentioned in a list of cancers that the authors speculate the antagonists might be useful for. No data are provided to support any suggestion that the compounds described therein would be effective in the treatment of pancreatic cancer on its own or in combination with any other therapy.

As mentioned above, the current inventors have found that antagonists of CCR1 are effective in treating pancreatic cancer, in particular when used in combination with other treatments.

The term "CCR1 antagonist" will be understood to mean an agent (e.g. a small molecule or CCR1-neutralising antibody) that antagonises the interaction of the chemokine receptor CCR1 and any one of its ligands. That is to say, the CCR1 antagonist is capable of inhibiting one or more of the processes normally triggered by the interaction of CCR1 with one of its ligands. Suitably, the CCR1 antagonist is an agent that antagonises the interaction of the IL1B, CCL1, CCL3, CCL5, CCl6, CCL7, CCL9, CCL15, CCL20 and/or CCL23 ligands. Most suitably, the CCR1 antagonist is an agent that antagonises the interaction of the IL1B, CCL1, CCL9 and/or CCL23 ligands, for example the CCL9 ligand.

In certain embodiments, the CCR1 antagonist is a CCR1-neutralising antibody. An example of a CCR1-neutralising antibody is antibody IgG1 (clone 141-2) available from MBL International (Woburn, Mass.). It will be appreciated that further antibodies can be realised using methods known in the art.

The current inventors have found CCR1 antagonists to be associated with minimal deleterious effects on non-cancerous cells. It has been observed that fibroblasts and macrophages treated with a CCR1 antagonist (BX471) appear to be just as viable as cell treated with vehicle control. Their use in human subjects is thus expected to be associated with fewer and less severe side effects than many other cancer treatments.

Preferably, the CCR1 antagonist is a small molecule antagonist, such as, for example those described hereinbelow. Suitably, the CCR1 antagonist is a small molecule CCR1 antagonist with a molecular weight of up to 1000 Da. Most suitably, the CCR1 antagonist is a small molecule CCR1 antagonist with a molecular weight of between 250 Da and 550 Da.

In certain embodiments, the CCR1 antagonist is selected from BL-5923, UCB-35625, BX-471, BI-638683, BI-639667, PS-031291, MLN-3701, AZD-4818, AZD-0492, MLN-3897, CP-481715, F-18-CCR1, AOP-RANTES, PS-375179, J113863, NSC-651016, and BAY-865047, BMS-817399, C-4462 and CCX-354, or a pharmaceutically acceptable salt, solvate or hydrate thereof (for example selected from BL-5923, UCB-35625, BX-471, BI-638683, BI-639667, PS-031291, MLN-3701, AZD-4818, AZD-0492, MLN-3897, CP-481715, F-18-CCR1, AOP-RANTES, PS-375179, J113863 and NSC-651016, or a pharmaceutically acceptable salt, solvate or hydrate thereof). Suitably, the CCR1 antagonist is selected from BL-5923, UCB-35625, BX-471, BI-638683, BI-639667, PS-031291, AZD-4818, AZD-0492, PS-375179, J113863 and NSC-651016, or a pharmaceutically acceptable salt, solvate or hydrate thereof. More suitably, the CCR1 antagonist is selected from UCB-35625, BX-471, BI-639667, AZD-4818, AZD-0492, and J113863, or a pharmaceutically acceptable salt, solvate or hydrate thereof. Even more suitably, the CCR1 antagonist is selected from BX-471, BI-639667, J113863, AZD-4818 or AZD-0492 or a pharmaceutically acceptable salt, solvate or hydrate thereof. Still more suitably, the CCR1 antagonist is selected from BX-471, BI-639667, J113863 or AZD-0492 or a pharmaceutically acceptable salt, solvate or hydrate thereof. Most suitably, the CCR1 antagonist is BX-471, or a pharmaceutically acceptable salt, solvate or hydrate thereof.

In certain embodiments, the CCR1 antagonist is selected from one of the following CCR1 antagonists: UCB-35625, BX-471 and J113863, or a pharmaceutically acceptable salt, solvate or hydrate thereof.

For example, the CCR1 antagonist is a piperazine-based CCR1 antagonist of the type described in WO03/035627 and/or US2003/0109534. Thus, in some embodiments, the CCR1 antagonist is a compound of Formula (I) shown below:

Formula (I)

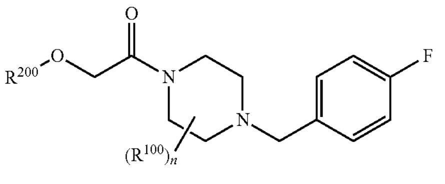

wherein:

n is an integer selected from 1, 2 or 3;

$R^{100}$ is a substituent group selected from alkly or hydroxyalkyl;

$R^{200}$ is a phenyl group substituted at the 4-position with a chloro group and substituted at the 2-position with an aminocarbonyl, ureido or glycinamido group;

or a pharmaceutically acceptable salt, solvate or hydrate thereof.

For example, the CCR1 antagonist is BX-471 ((2R)-1-[[2-[(Aminocarbonyl)amino]-4-chlorophenoxy]acetyl]-4-[(4-fluorophenyl)methyl]-2-methylpiperazine), shown below:

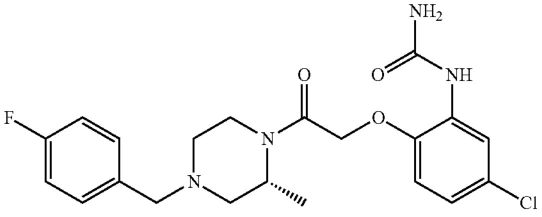 [SMILES: C[C@@H]1CN(Cc2ccc(F)cc2)CCN1C(=O)COc1ccc(Cl)cc1NC(N)=O]

or a pharmaceutically acceptable salt, solvate or hydrate thereof.

For example, the CCR1 antagonist is a spirocyclic piperidine based CCR1 antagonist as described in WO2008/103126. That is to say, in some embodiments, the CCR1 antagonist is a compound of Formula (II) shown below:

Formula (II)

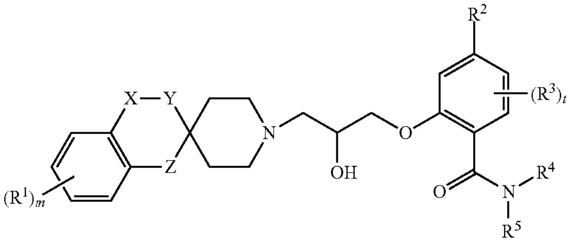

wherein:

m is 1;

t is 1;

$R^1$ is halogen;

X, Y and Z are independently a bond, —O— or —$CH_2$—, provided that only one of X, Y and Z is a bond;

$R^2$ is $C_{1-6}$alkoxy, optionally substituted by one or more substituent groups independently selected from hydroxyl and carboxyl;

$R^3$ is a halogen;

$R^4$ and $R^5$ are independently selected from hydrogen and $C_{1-6}$ alkyl;

or a pharmaceutically acceptable salt, solvate or hydrate thereof.

For example, the CCR1 antagonist is AZD-4818 ((2-[2-Chloro-5-[(2S)-3-(5-chlorospiro[benzofuran-2(3H),4'-piperidin]-1'-yl)-2-hydroxypropoxy]-4-[(methylamino)carbonyl]phenoxy]-2-methylpropanoic acid), shown below:

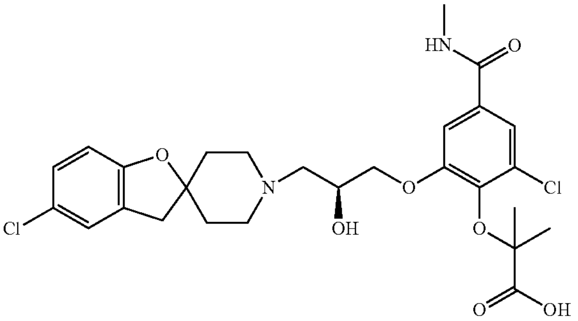 [SMILES: CNC(=O)c1cc(Cl)c(OC(C)(C)C(=O)O)c(OC[C@@H](O)CN2CCC3(CC2)Cc2cc(Cl)ccc2O3)c1]

or a pharmaceutically acceptable salt, solvate or hydrate thereof.

For example, the CCR1 antagonist is a 2,7-dichloro-9H-xanthen-9-yl based CCR1 antagonist as described in EP0916668A1. That is to say, in some embodiments, the CCR1 antagonist is a compound of Formula (III) shown below:

Formula (III)

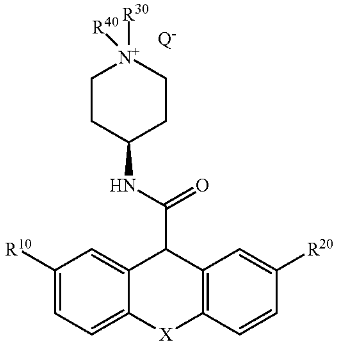

wherein:

$R^{10}$ and $R^{20}$ are independently selected from a hydrogen atom, a halogen atom or a $C_{1-6}$ alkly;

X is —O—, —S— or —$CH_2$—;

Q is an anion (e.g. $Cl^-$, $Br^-$ or $I^-$);

$R^{30}$ is a cyclooctylmethyl group, a cyclononylmethyl group, a 1-decalylmethyl group, a 2-decalylmethyl group, a (1-cyclooctenyl)methyl group or a (1-cyclononenyl)methyl group;

$R^{40}$ is selected from a methyl, ethyl, propyl or allyl;

or a pharmaceutically acceptable salt, solvate or hydrate thereof.

For example, the CCR1 antagonist is a 2,7-dichloro-9H-xanthen-9-yl based CCR1 antagonist as described in EP0916668A1. That is to say, in some embodiments, the CCR1 antagonist is a compound of Formula (III) shown below or a pharmaceutically acceptable salt, solvate or hydrate thereof:

Formula (III)

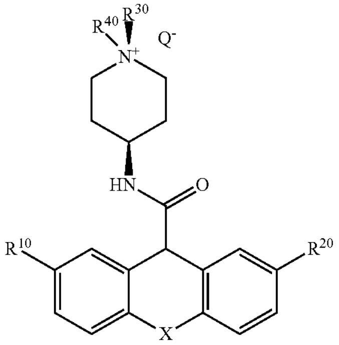

wherein $R^{10}$, $R^{20}$, X, Q, $R^{30}$ and $R^{40}$ are as defined above.

For example, the CCR1 antagonist is J113863 (1,4-cis-1-(1-cycloocten-1-ylmethyl)-4-[[(2,7-dichloro-9H-xanthen-9-yl)carbonyl]amino]-1-ethylpiperidinium iodide), shown below:

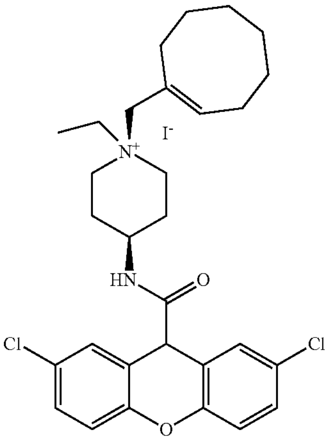 [SMILES: CC[N@+]1(C/C2=C/CCCCCC2)CC[C@@H](NC(=O)C2c3cc(Cl)ccc3Oc3ccc(Cl)cc32)CC1 ; [I-]]

or a pharmaceutically acceptable salt, solvate or hydrate thereof.

The present invention encompasses all pharmaceutically acceptable salts of the CCR1 antagonist described herein. A suitable pharmaceutically acceptable salt of a CCR1 antagonist of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a CCR1 antagonist of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

The present invention also encompasses CCR1 antagonist of the invention as defined herein which comprise one or more isotopic substitutions. For example, H may be in any isotopic form, including 1H, 2H(D), and 3H (T); C may be in any isotopic form, including 12C, 13C, and 14C; and O may be in any isotopic form, including 16O and 18O; and the like.

It is also to be understood that certain CCR1 antagonists of the present invention may exist in solvated as well as unsolvated forms such as, for example, hydrated forms. It is to be understood that the invention encompasses all such solvated forms that possess anticancer activity.

It is also to be understood that certain CCR1 antagonists, may exhibit polymorphism, and that the invention encompasses all such forms that possess anticancer activity.

The CCR1 antagonists may also be administered in the form of a pro-drug which is broken down in the human or animal body to release a CCR1 antagonist of the invention. A pro-drug may be used to alter the physical properties and/or the pharmacokinetic properties of the CCR1 antagonist. A pro-drug can be formed when the CCR1 antagonist contains a suitable group or substituent to which a property-modifying group can be attached. Examples of pro-drugs include in vivo cleavable ester derivatives that may be formed at a carboxy group or a hydroxy groups in the CCR1 antagonist, and in vivo cleavable amide derivatives that may be formed at a carboxy group or an amino group in the CCR1 antagonist.

Methods of Treatment

The invention provides a method of treating pancreatic cancer in a subject in need of such treatment, said method comprising administering to said subject a therapeutically effective amount of a CCR1 antagonist, a pharmaceutically acceptable salt, solvate or hydrate thereof, or a pharmaceutical composition thereof.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

The method of treating pancreatic cancer in accordance with the invention a subject in need of such treatment, is especially effective in the treatment of pancreatic cancer when it is carried out in combination with an established treatment regimen, such as a treatment often referred to as 'standard of care'. Such combinations are discussed in further detail below. In a preferred embodiment, there is provided a method of treating pancreatic cancer comprising administering to said subject a therapeutically effective amount of a CCR1 antagonist, a pharmaceutically acceptable salt, solvate or hydrate thereof, or a pharmaceutical composition thereof in combination with one or more chemotherapeutic agents selected from Gemcitabine (Gemzar®), Fluorouracil (5-FU), Capecitabine (Xeloda®), FOLFIRINOX and Nab-paclitaxel (Abraxane®).

The CCR1 antagonist may further, or alternatively be used in combination with an immuno-oncology agent (e.g. PD-1 and/or a PD-L1 inhibitor).

The CCR1 antagonist may further, or alternatively be used in combination with an MEK inhibitor.

As mentioned above, the present inventors have found a strong correlation between the level of CCR1 expressed in pancreatic cancer cells (e.g. PDAC cells) and patient prognosis. The method of treatment of the present invention is thus, in one embodiment, a method of treating pancreatic cancer in a subject who has been identified as having increased levels of CCR1 expression compared to a reference expression level.

As mentioned above, the present inventors have found a strong correlation between the level of immune (e.g. macrophage) infiltration and patient prognosis. The method of treatment of the present invention is thus, in one embodiment, a method of treating pancreatic cancer in a subject in whom increased levels of immune (e.g. macrophage) infiltration have been identified compared to a reference infiltration level.

As also mentioned herein, the current inventors have found a correlation between the level of the biomarkers PIM3, GSK3B, ATK1, CDK1, CDK5, MAPK14, MTOR, MAPK3, CAMK2A, MAP2K1, MAPK8, PRKACA, SRC, RPS6KA1, MAPK1 and PRKCA and poor patient prognosis. These kinases and genes in the AKT/MAPK pathways are commonly associated with poor prognosis in multiple cancers. The method of treatment of the present invention is thus, in one embodiment, a method of treating pancreatic cancer in a subject in whom an increased level of at least one biomarker selected from PIM3, GSK3B, ATK1, CDK1, CDK5, MAPK14, MTOR, MAPK3, CAMK2A, MAP2K1, MAPK8, PRKACA, SRC, RPS6KA1, MAPK1 and PRKCA has been identified.

A "therapeutically effective amount" means the amount of a compound that, when administered to a mammal for treating a disease, is sufficient to effect such treatment for the disease. The "therapeutically effective amount" will vary depending on the compound, the disease and its severity, the age, weight, etc., of the mammal to be treated, and/or the size of tumour imaged and/or scanned. Suitably, the "therapeutically effective amount" will vary depending on the size of tumour imaged and/or scanned. A medical practitioner will be suitably qualified to determine the "therapeutically effective amount" in view of the factors outlined above (e.g. the size of tumour imaged and/or scanned). The current standard of care treatments described below have associated with them established best dosing regimens and those are also appropriate when the treatments are used in a combination as A "subject" of the present invention will be understood to mean a human and/or animal subject.

It will be understood that the term "pancreatic cancer" encompasses all forms of cancer of the pancreas. That is to say, the pancreatic cancer may be cancer of the exocrine gland (e.g. pancreatic ductal adenocarcinomas) and/or cancer of the endocrine gland (e.g. pancreatic neuroendocrine tumours). It will also be understood that the term "pancreatic cancer" may also encompass cancer which has spread to the pancreas from malignant tumours originating elsewhere in the body (e.g. liver, peritoneum, lung, adrenal and bone).

Pancreatic cancer is typically classified by the size and location of the cancer within the body. Stage 1 pancreatic cancer is the earliest form of pancreatic cancer, and describes situations in which the cancer cells are predominately contained within the pancreas. Stage 1 pancreatic cancer is often referred to as early, localised or resectable pancreatic cancer (which refers to the fact that the cancer can often be removed by surgery). Stage 2 pancreatic cancer is the descriptor used when the cancer cells have spread from the pancreas to, for example, the duodenum, bile duct or tissues directly surrounding the pancreas. Some forms of Stage 2 pancreatic cancer is resectable. Stage 3 pancreatic cancer is the descriptor used when the cancer cells have spread from the pancreas into the stomach, spleen, large bowel or the large blood vessels near the pancreas. Stage 3 pancreatic cancer is not often resectable. Stage 4 pancreatic cancer is the descriptor used when the cancer cells have spread from the pancreas to parts of the body such as the lungs, liver or peritoneum. Stage 4 pancreatic cancer is unresectable.

In certain embodiments, the pancreatic cancer is Stage 3 or Stage 4 pancreatic cancer, suitably, Stage 4 pancreatic cancer.

In further embodiments, the pancreatic cancer is pancreatic ductal adenocarcinoma (PDAC), and suitably, Stage 4 pancreatic ductal adenocarcinoma (PDAC).

It will be understood that an effective amount of a CCR1 antagonist for use in the treatment of pancreatic cancer is an amount sufficient to treat, prevent or cure the proliferative of the pancreatic cancer, slow its progression and/or reduce the symptoms associated with the pancreatic cancer.

The amount of active ingredient (e.g. CCR1 antagonist) that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic (or prophylactic) purposes of the CCR1 antagonist will naturally vary according to the nature and severity of the conditions, the age and sex of the animal or patient and the route of administration, according to well-known principles of medicine.

In using a CCR1 antagonist for the treatment of pancreatic cancer it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of CCR1 antagonist.

Diagnosis of a Pancreatic Cancer Patient:

In the diagnosis of a pancreatic cancer in the subject, the expression levels of CCR1 may be determined by any suitable means known in the art. For example, the level of expression of CCR1 may be determined by measuring CCR1 protein levels. The CCR1 protein levels may be measured using any suitable technique known in the art, such as, for example, SDS-PAGE followed by Western blot using suitable antibodies raised against the target protein, by proteomics, membrane spot arrays or by immunohistochemical (IHC) methods. In addition, or alternatively, the level of expression of CCR1 may be determined by measuring the level of mRNA. The level of mRNA may be measured using any suitable technique known in the art, such as, for example, northern blot, imaging mass cytometry (IMC), RNA sequencing (RNAseq), single cell RNA sequencing (scRNAseq) or quantitative RT-PCR (qRT-PCR). The analysis may be carried out on a biopsy taken from the subject. In each case, the measured level in the sample may be compared to a reference expression level.

It will be appreciated that the immune (e.g. macrophage) infiltration may be determined using any suitable technique known in the art. A non-limiting list of possible techniques for determining macrophage infiltration level include immunofluorescence (IF), immunohistochemical (IHC), imaging mass cytometry (IMC), flow cytometry, RNA sequencing (RNAseq), single cell RNA sequencing (scRNAseq) or proteomics.

The test score may be calculated by applying the Immune Score metric (as described in the example section hereinbelow) to the expression level data. Suitably, the Immune Score is calculated by employing a single-sample gene set enrichment analysis (ssGSEA) to the expression data to calculate a normalised enrichment score (NES). Most suitably, the Immune Score is be calculated by employing "Estimation of STromal and Immune cells in Malignant Tumours using Expression data" (ESTIMATE, Nature Comm., 2013, 4(2612), 1-11), a single-sample gene set enrichment analysis (ssGSEA)-based method, to the expression data.

The pre-determined threshold score represents a pre-determined Immune Score generated from a reference sample set of pancreatic cancer patients. Suitably, the pre-determined threshold score represents a pre-determined Immune Score generated from a reference sample set of stage IV pancreatic cancer (PDAC) patients.

The pre-determined threshold score may be derived using any suitable method known in the art. Suitably, the pre-determined threshold score is derived from expression data from a reference sample set of pancreatic cancer patients. The reference sample set may be, for example, a sample of pancreatic cancer patients (e.g. stage IV pancreatic cancer patients) for which expression data has been generated. Non-limiting examples of suitable reference sample sets include, for example, expression data for pancreatic cancer patients (e.g. stage IV pancreatic cancer patients) that is available on The Cancer Genome Atlas (TCGA), or similar databases (e.g. the databases of the International Cancer Genome Consortium (ICDC), UT Southwestern Medical Centre and Queensland Centre for Medical Genomics (QCMG)). Thus, the pre-determined threshold score may be generated using expression data from pancreatic cancer patients (e.g. stage IV pancreatic cancer patients) that is available on from The Cancer Genome Atlas (TCGA), by employing "Estimation of STromal and Immune cells in Malignant Tumours using Expression data" (ESTIMATE), a single-sample gene set enrichment analysis (ssGSEA)-based method, to said expression data.

Suitably, the pre-determined threshold score is an Immune Score that corresponds to the $25^{th}$ percentile of the Immune Scores generated from the reference sample set.

Suitably, the method involves treating the subject if the test score (e.g. Immune Score) is greater than the $25^{th}$ percentile of the Immune Scores generated from the reference sample set (i.e. the pre-determined threshold score).

For example, the subject in need of treatment is a subject who has been diagnosed with pancreatic cancer and has been identified as having one or more of the following:

- increased levels of expression of CCR1 compared to a reference expression level;
- increased levels of immune (e.g. macrophage) infiltration compared to a reference infiltration level;
- high levels of MYC expression and/or a mutation of the MYC oncogene;
- an SMAD4 mutation; and/or
- a classical Moffitt's tumour RNA subtype.

The term "MYC" used herein will be understood to mean the whole family of regulator genes (transcriptional factors) that fall within the MYC gene family. Members of the MYC transcription factor family include c-MYC, MYCN and MYCL, and thus reference to "MYC" herein will be understood to covers all of such family members. MYC regulator genes encode a family of transcription factors involved in cell proliferation, growth, differentiation and apoptosis. Activation of normal MYC genes affects numerous cellular processes, including cell cycle progression, cell growth and division, metabolism, telomerase activity, adhesion and motility, angiogenesis and differentiation. MYC, has been identified as a strong proto-oncogene and its mutated versions are often found to be upregulated and/or constitutively expressed in certain types of cancers, such as haematological cancers and solid tumour malignancies (Miller et al., Clin. Cancer Res., 2012, 18(20), 5546-5553). Thus, a subject who has been diagnosed with pancreatic cancer and has been identified as having high MYC expression and/or a mutation of the MYC oncogene is likely to a subject who will respond worse to the standard of care for pancreatic cancer, and will therefore likely have a poorer progression-free survival rate.

An important genetic change in pancreatic cancer is the SMAD4 mutation, which leads to the loss of SMAD4 protein expression. SMAD4 is a tumour suppressor gene that is inactivated in more than 50% of pancreatic cancer cases. Many studies have shown that the loss of SMAD4 expression is positively associated with poor prognosis in pancreatic cancer patients (Wei et al., Transl. Oncol. 2016, 9(1), 1-7). Thus, a subject who has been diagnosed with pancreatic cancer and has been identified as having an SMAD4 mutation is a subject who is likely to have a higher need and poorer progression-free survival rate.

Combination Therapy

In an important aspect of the present invention, there is provided a CCR1 antagonist, pharmaceutically acceptable salt, solvate or hydrate thereof, in combination with one or more standard pancreatic cancer treatment regimens, for use in the treatment of pancreatic cancer.

It will be appreciated that the one or more standard pancreatic cancer treatment regimens may be any suitable treatment regimen commonly employed to treat pancreatic cancer (i.e. the "standard of care" for pancreatic cancer). Suitably, the one or more standard pancreatic cancer treatment regimens are selected from surgery, radiotherapy, chemotherapy, immunotherapy and a combination thereof. More suitably, the standard pancreatic cancer treatment regimen is selected from surgery, chemotherapy or immunotherapy and a combination thereof. Most suitably, the standard pancreatic cancer treatment regimen comprises chemotherapy and optionally one or more additional treatment regimens selected from surgery and immunotherapy.

For pancreatic cancer patients diagnosed with early stage pancreatic cancer (stage I or II), the standard pancreatic cancer treatment regimen comprises surgery and optionally one or more additional treatment regimens selected from chemotherapy and immunotherapy. For example, the UK's National Institute for Clinical Excellence recommends for non-metastatic or otherwise not sufficiently 'locally advanced' that pancreatic cancer is treated by surgery followed by adjuvant chemotherapy. The first recommendation is for the combination of gemcitabine+capecitabine for 6 treatment cycles; if the combination therapy is not tolerated, then gemcitabine alone.

For pancreatic cancer patients diagnosed with late stage pancreatic cancer (stage III or IV), the standard pancreatic cancer treatment regimen comprises chemotherapy and optionally one or more additional treatment regimens selected from surgery and immunotherapy. For example, the UK's National Institute for Clinical Excellence recommends for locally advanced or metastatic pancreatic cancer that it be treated by chemotherapy or chem radiotherapy. For locally advanced pancreatic cancer, the first recommendation is systemic combination chemotherapy (for example the FOLFIRINOX combination discussed below). If combinations are not tolerated, then gemcitabine alone. If chemradiotherapy is used, then capecitabine should be given. A variant of FOLFIRINOX is mFOLFIRINOX; that has no initial injection/bolus of fluorouracil and the irinotecan level is decreased to 150 $mg/m^2$. Further treatment options, recommended by the US Clinical practice guidelines for pancreatic cancer in the USA include novel inhibitors e.g. erlotinib, capecitabine or taxanes (such as docetaxel).

For metastatic pancreatic cancer, the first recommendation is treatment with FOLFIRINOX (it has the best survival statistics, but is most poorly tolerated). If FOLFIRINOX is not tolerated, then gemcitabine+nab-paclitaxel should be given. If no combinations are tolerated, gemcitabine alone should be given. Further treatment options, recommended by the US Clinical practice guidelines for pancreatic cancer in the USA, include the addition of further novel agents pembrolizumab, larotrectinib or entrectinib.

Metastatic 2nd-line therapy is a Gemcitabine-based regimen (after 1st line FOLFIRINOX), or an Oxaliplatin-based regimen (after other 1st line combinations). A nanoliposomal combination of irinotecan+fluorouracil+folinic acid is recommended as a second line therapy in the European Society of Medical Oncology (ESMO) clinical practice guidelines (after 1st line gemcitabine-based therapy). Further treatment options, recommended by the US Clinical practice guidelines for pancreatic cancer in the USA, include capecitabine or fluorouracil alone, and the addition of further novel agents pembrolizumab, larotrectinib or entrectinib.

Surgery may be the surgical intervention by a medical practitioner to remove the whole or part of a tumour.

Radiotherapy may be any form of treatment utilising ionizing radiation. Non-limiting examples of suitable radiotherapy treatments include, for example, external beam radiotherapy (EBRT), stereotactic radiosurgery (STRS) and teletherapy.

Chemotherapy may be a treatment by administration of one or more anti-tumour (anti-cancer) agents. As mentioned above, non-limiting examples of suitable anti-tumour agents for the treatment of pancreatic cancer include Gemcitabine (Gemzar®), Fluorouracil (5-FU), Capecitabine (Xeloda®), FOLFIRINOX (Leucovorin Calcium, Fluorouracil, Irinotecan Hydrochloride and Oxaliplatin) and Nab-paclitaxel (Abraxane®).

Gemcitabine, 5-fluorouracil, and capecitabine are pyrimidine antagonists (also sometimes broadly classed as antimetabolites).

Immunotherapy (immune-oncology) may be any form of treatment which exploits the patient's immune system. Non-limiting examples of suitable immunotherapeutic treatment includes, for example, treatments utilising one or more of the following: monoclonal antibodies (MABs); vaccinations; cytokines; and CAR T-cells. Suitably, immunotherapy (immune-oncology) comprises the administration of a PD-L1 inhibitor and/or a PD-1 inhibitor. Non-limiting examples of suitable PD-1 inhibitors include pembrolizumab, nivolumab, IBI-308, mDX-400, BGB-108, MEDI-0680, SHR-1210, PF-06801591, PDR-001, GB-226 and STI-1110. Non-limiting examples of suitable PD-L1 inhibitors include durvalumab, atezolizumab, avelumab, BMS-936559, ALN-PDL, TSR-042, KD-033, CA-170, STI-1014 and KY-1003.

Suitably, the PD-1 inhibitor is selected from pembrolizumab or nivolumab. Most suitably, the PD-1 inhibitor is nivolumab.

In summary therefore, the standard pancreatic cancer treatment regimen for pancreatic cancer (e.g. stage I or II pancreatic cancer) may comprise surgery to remove part or all of the tumour, followed by the administration of a chemotherapeutic agent selected from Gemcitabine (Gemzar®), Fluorouracil (5-FU), Capecitabine (Xeloda®), FOLFIRINOX, Nab-paclitaxel (Abraxane®) or a combination thereof. Similarly, the standard tumour treatment regimen for pancreatic cancer at stage III or IV comprises the administration of a chemotherapeutic agent selected from Gemcitabine (Gemzar®), Fluorouracil (5-FU), Capecitabine (Xeloda®), FOLFIRINOX, Nab-paclitaxel (Abraxane®) or a combination thereof.

In a preferred treatment in accordance with the invention, a CCR1 antagonist (e.g. BX-471), or pharmaceutically acceptable salt, solvate or hydrate thereof, is used in combination with an established therapy for pancreatic cancer.

Considering the standard of care regimens that are currently recommended, the CCR1 antagonist is suitably used in combination with a chemotherapeutic agent selected from Gemcitabine or Capecitabine, particularly Gemcitabine. The inventors have seen an especially strong therapeutically beneficial effect in a mouse model when a CCR1 antagonist was administered with Gemcitabine.

In a further particular combination therapy, the CCR1 antagonist is used in combination with FOLFIRINOX. It may also be used in combination with oxaliplatin. It may also be used in combination with Nab-paclitaxel. It may also be used in combination with an immunotherapy, such as a PD-1 or PD-L1 inhibitor.

Further novel therapies are being developed and the CCR1 antagonist may also suitably be used those. Thus the CCR1 antagonist may be used in combination with erlotinib, capecitabine taxanes (such as docetaxel), pembrolizumab, larotrectinib or entrectinib.

An especially suitable combination therapy is the CCR1 antagonist administered with Gemcitabine (for example in the FOLFIRINOX combination) and a PD-1 inhibitor. The inventors have seen an especially strong therapeutically beneficial effect in a mouse model when a CCR1 antagonist was administered with Gemcitabine and a PD-1 inhibitor. A combination treatment of a CCR1 antagonist, Gemcitabine and a PD-1 inhibitor is thus preferred. Nab-paclitaxel can optionally also be included.

A further especially suitable combination therapy is the CCR1 antagonist administered with FOLFIRINOX and a PD-1 inhibitor. A combination treatment of a CCR1 antagonist, FOLFIRINOX and a PD-1 inhibitor is thus preferred. Nab-paclitaxel can optionally also be included.

For example, the CCR1 antagonist is used in combination with one or more chemotherapeutic agents selected from Gemcitabine (Gemzar®), Fluorouracil (5-FU), Capecitabine (Xeloda®), FOLFIRINOX and Nab-paclitaxel (Abraxane®), in the treatment of pancreatic cancer. Suitably, there is provided a CCR1 antagonist (e.g. BX-471), or pharmaceutically acceptable salt, solvate or hydrate thereof, in combination with one or more chemotherapeutic agents selected from Gemcitabine (Gemzar®), Nab-paclitaxel (Abraxane®), FOLFIRINOX or combinations thereof. More suitably, there is provided a CCR1 antagonist (e.g. BX-471), or pharmaceutically acceptable salt, solvate or hydrate thereof, in combination Gemcitabine (Gemzar®) and/or Nab-paclitaxel (Abraxane®), for use in the treatment of pancreatic cancer. Most suitably, there is provided a CCR1 antagonist (e.g. BX-471), or pharmaceutically acceptable salt, solvate or hydrate thereof, in combination with Gemcitabine (Gemzar®), for use in the treatment of pancreatic cancer.

In another aspect of the present invention, there is provided a CCR1 antagonist (e.g. BX-471), or pharmaceutically acceptable salt, solvate or hydrate thereof, in combination with a chemotherapeutic agent selected from Gemcitabine (Gemzar®), Fluorouracil (5-FU), Capecitabine (Xeloda®), FOLFIRINOX and Nab-paclitaxel (Abraxane®); and optionally, one or more of the following agents: an MEK inhibitor, an IGF1R inhibitor, a PD-1 inhibitor, a PD-L1 inhibitor and/or a immuno-oncology agent (e.g. PD-1 and/or a PD-L1 inhibitor), for use in the treatment of pancreatic cancer.

In another aspect of the present invention, there is provided a CCR1 antagonist (e.g. BX-471), or pharmaceutically acceptable salt, solvate or hydrate thereof, in combination with a chemotherapeutic agent selected from Gemcitabine (Gemzar®), Fluorouracil (5-FU), Capecitabine (Xeloda®), FOLFIRINOX and Nab-paclitaxel (Abraxane®); and optionally, one or more immuno-oncology agents (e.g. PD-1 and/or a PD-L1 inhibitor), for use in the treatment of pancreatic cancer.

For example, the chemotherapeutic agents are administered simultaneously, and the one or more immuno-oncology agents are administered sequentially thereafter.

For example, the chemotherapeutic agents and the one or more immuno-oncology agents are administered sequentially. It will be understood that the CCR1 antagonist, the chemotherapeutic agent and the one or more immuno-oncology agents may be administered in any sequential order. Suitably, the CCR1 antagonist is administered first, followed by the sequential administration of the chemotherapeutic agent and the one or more immuno-oncology agents.

In another aspect of the present invention, there is provided a CCR1 antagonist (e.g. BX-471), or pharmaceutically acceptable salt, solvate or hydrate thereof, in combination with;

a MEK inhibitor and/or an IGF1R inhibitor; and optionally a chemotherapeutic agent selected from Gemcitabine (Gemzar®), Fluorouracil (5-FU), Capecitabine (Xeloda®), FOLFIRINOX and Nab-paclitaxel (Abraxane®);

for use in the treatment of pancreatic cancer.

In another aspect of the present invention, there is provided a CCR1 antagonist (e.g. BX-471), or pharmaceutically acceptable salt, solvate or hydrate thereof, in combination with;

a PD-1 or PD-L1 inhibitor; and optionally a chemotherapeutic agent selected from Gemcitabine (Gemzar®), Fluorouracil (5-FU), Capecitabine (Xeloda®), FOLFIRINOX and Nab-paclitaxel (Abraxane®);

for use in the treatment of pancreatic cancer.

In another aspect of the present invention, there is provided a CCR1 antagonist (e.g. BX-471), pharmaceutically acceptable salt, solvate or hydrate thereof, in combination with a MEK inhibitor and/or an IGF1R inhibitor, for use in the treatment of pancreatic cancer.

Non-limiting examples of suitable MEK inhibitors include CI-1040 (PD184352), PD0325901, Selumetinib (AZD6244), MEK162, AZD8330, TAK-733, GDC-0623, Refametinib (RDEA119, BAY869766), Pimasertib (AS703026), RO4987655 (CH4987655), RO5126766, WX-554, HL-085 and combinations thereof (Tian et al., Molecules, 2017, 22(10), 1551).

Non-limiting examples of suitable IGF1R inhibitors include Dalotuzumab (and combinations of Dalotuzumab with one or more of MK-2206, ridaforolimus, MK-0752, cetuximab, irinotecan, cisplatin etoposide and erlotinib) Figitumumab (and combinations of Figitumumab with one or more of carboplatin, paclitaxel, dexamethasone, docetaxel, prednisone, erlotinib and everolimus), Gantitumab (and combinations of Gantitumab with one or more of exemestane, fulvestrant, FOLFIRI, gemcitabine, panitumumab, sorafenib and erlotinib), Linsitinib (and combinations of Linsitinib with everolimus) and R1507 (Yee et al., Molecular Endocrinology, 2015, 29(11), 1549-1557).

In a further aspect of the present invention, there is provided a CCR1 antagonist (e.g. BX-471), or pharmaceutically acceptable salt, solvate or hydrate thereof, in combination with one or more of the following agents:

- an MEK inhibitor
- an IGF1R inhibitor;
- a PD-1 or PD-L1 inhibitor; and/or
- a chemotherapeutic agent selected from Gemcitabine (Gemzar®), Fluorouracil (5-FU), Capecitabine (Xeloda®), FOLFIRINOX and Nab-paclitaxel (Abraxane®)

for use in the treatment of pancreatic cancer in a subject in need of such treatment, wherein said subject is a subject who has been diagnosed with pancreatic cancer and has been identified as having:

- increased levels of expression of CCR1 compared to a reference expression level; and/or
- increased levels of immune (e.g. macrophage) infiltration compared to a reference infiltration level.

In an embodiment, the present invention provides a CCR1 antagonist (e.g. BX-471), or pharmaceutically acceptable salt, solvate or hydrate thereof, in combination with one or more of the following agents:

- a MEK inhibitor
- an IGF1R inhibitor;
- a PD-1 or PD-L1 inhibitor; and/or
- a chemotherapeutic agent selected from Gemcitabine (Gemzar®), Nab-paclitaxel (Abraxane®), FOLFIRINOX or combinations thereof;

for use in the treatment of pancreatic cancer in a subject in need of such treatment, wherein said subject is a subject who has been diagnosed with pancreatic cancer and has been identified as having:

- increased levels of expression of CCR1 compared to a reference expression level;
- increased levels of immune (e.g. macrophage) infiltration compared to a reference infiltration level;
- high levels of MYC expression and/or a mutation of the MYC oncogene;
- a SMAD4 mutation; and/or
- a classical Moffitt's tumour RNA subtype.

In certain embodiments, the subject is a subject who has been diagnosed with pancreatic cancer and has been identified as having a test score that is greater than the predetermined threshold score (e.g. the $25^{th}$ percentile of Immune Scores generated from the reference sample set), as determined by the method of the present invention defined hereinabove.

In yet another aspect of the present invention, there is provided a method of treating pancreatic cancer in a subject in need of such treatment, said method comprising administering to said subject a therapeutically effective amount of a CCR1 antagonist (e.g. BX-471), or pharmaceutically acceptable salt, solvate or hydrate thereof, or a pharmaceutical composition thereof, in combination with one or more chemotherapeutic agents selected from Gemcitabine (Gemzar®), Fluorouracil (5-FU), Capecitabine (Xeloda®), FOLFIRINOX and Nab-paclitaxel (Abraxane®).

In some embodiments, there is provided a method of treating pancreatic cancer (e.g. stage IV pancreatic cancer) in a subject in need of such treatment, said method comprising administering to said subject a therapeutically effective amount of a CCR1 antagonist (e.g. BX-471), or pharmaceutically acceptable salt, solvate or hydrate thereof, or a pharmaceutical composition thereof, in combination with one or more chemotherapeutic agents selected from Gemcitabine (Gemzar®), Nab-paclitaxel (Abraxane®), FOLFIRINOX or combinations thereof, and optionally one or more immuno-oncology agents (e.g. PD-1 and/or a PD-L1 inhibitor).

In still another aspect of the present invention, there is provided a method of treating pancreatic cancer in a subject in need of such treatment, said method comprising administering to said subject a therapeutically effective amount of a CCR1 antagonist (e.g. BX-471), or pharmaceutically acceptable salt, solvate or hydrate thereof, or a pharmaceutical composition thereof, in combination with an MEK inhibitor and/or an IGF1R inhibitor, and optionally one or more chemotherapeutic agents selected from Gemcitabine (Gemzar®), Fluorouracil (5-FU), Capecitabine (Xeloda®), FOLFIRINOX and Nab-paclitaxel (Abraxane®).

In some embodiments, there is provided a method of treating pancreatic cancer (e.g. stage IV pancreatic cancer) in a subject in need of such treatment, said method comprising administering to said subject a therapeutically effective amount of a CCR1 antagonist (e.g. BX-471), or pharmaceutically acceptable salt, solvate or hydrate thereof, or a pharmaceutical composition thereof, in combination with an MEK inhibitor and/or an IGF1R inhibitor, and optionally one or more chemotherapeutic agents selected from Gemcitabine (Gemzar®), Nab-paclitaxel (Abraxane®), FOLFIRINOX or combinations thereof.

In a further aspect of the present invention, there is provided a method of treating pancreatic cancer in a subject in need of such treatment, said method comprising administering to said subject a therapeutically effective amount of a CCR1 antagonist (e.g. BX-471), or pharmaceutically acceptable salt, solvate or hydrate thereof, or a pharmaceutical composition thereof, in combination with one or more of the following agents:

- an MEK inhibitor
- an IGF1R inhibitor;
- a PD-1 or PD-L1 inhibitor; and/or
- a chemotherapeutic agent selected from Gemcitabine (Gemzar®), Fluorouracil (5-FU), Capecitabine (Xeloda®), FOLFIRINOX and Nab-paclitaxel (Abraxane®);

wherein the subject in need of treatment is a subject who has been identified as having:

- increased levels of expression of CCR1 compared to a reference expression level; and/or
- increased levels of immune (e.g. macrophage) infiltration compared to a reference infiltration level.

In certain embodiments, there is provided a method of treating pancreatic cancer (e.g. stage IV pancreatic cancer) in a subject in need of such treatment, said method comprising administering to said subject a therapeutically effective amount of a CCR1 antagonist (e.g. BX-471), or pharmaceutically acceptable salt, solvate or hydrate thereof, or a pharmaceutical composition thereof, in combination with one or more of the following agents:

- an MEK inhibitor
- an IGF1R inhibitor;
- a PD-1 or PD-L1 inhibitor; and/or
- a chemotherapeutic agent selected from Gemcitabine (Gemzar®), Nab-paclitaxel (Abraxane®), FOLFIRINOX or combinations thereof;

wherein the subject in need of treatment is a subject who has been identified as having one or more of the following:

- increased levels of expression of CCR1 compared to a reference expression level;
- increased levels of immune (e.g. macrophage) infiltration compared to a reference infiltration level;

high levels of MYC expression and/or a mutation of the MYC oncogene;

a SMAD4 mutation; and/or a classical Moffitt's tumour RNA subtype.

More suitably, there is provided a method of treating pancreatic cancer (e.g. stage IV pancreatic cancer) in a subject in need of such treatment, said method comprising administering to said subject a therapeutically effective amount of a CCR1 antagonist (e.g. BX-471), or pharmaceutically acceptable salt, solvate or hydrate thereof, or a pharmaceutical composition thereof, in combination with a chemotherapeutic agent selected from Gemcitabine (Gemzar®), Fluorouracil (5-FU), Capecitabine (Xeloda®), FOLFIRINOX and Nab-paclitaxel (Abraxane®), and optionally, in combination with one or more of the following agents:

an MEK inhibitor;

an IGF1R inhibitor; and/or a PD-1 or PD-L1 inhibitor;

wherein the subject has been identified as having:

increased levels of expression of CCR1 compared to a reference expression level; and/or increased levels of immune (e.g. macrophage) infiltration compared to a reference infiltration level;

and optionally, the subject in need of treatment is a subject who has been identified as having one or more of the following high levels of MYC expression and/or a mutation of the MYC oncogene;

a SMAD4 mutation; and/or a classical Moffitt's tumour RNA subtype.

In certain embodiments, the subject is a subject who has been diagnosed with pancreatic cancer and has been identified as having a test score that is greater than the predetermined threshold score (e.g. the $25^{th}$ percentile of Immune Scores generated from the reference sample set), as determined by the method of the present invention defined hereinabove.

It will be appreciated that the combinations described herein may be sequential, separate and/or simultaneous combinations of the listed agents. That is to say, the listed agents may be added at the same time or separately. In situations where the combination comprises more than two agents, the combination may comprise the sequential, separate and/or simultaneous administration of all of the listed agents, or the combination may comprise the sequential administration of some agents and the simultaneous administration of other agents. In certain embodiments, the combinations described herein are sequential combinations, wherein the listed agents are administered in sequence (e.g. one after the other). In other embodiments, the combinations described herein are simultaneous combinations, wherein the listed agents are administered together.

Pharmaceutical Compositions

According to another aspect of the present invention, there is provided a pharmaceutical composition which comprises a CCR1 antagonist as defined hereinbefore, or a pharmaceutically acceptable salt, hydrate or solvate thereof, in association with a pharmaceutically acceptable diluent or carrier, for use in the treatment of pancreatic cancer.

The invention provides a pharmaceutical composition comprising a CCR1 antagonist together one or more additional therapeutic agents selected from:

an MEK inhibitor an IGF1R inhibitor;

a PD-1 or PD-L1 inhibitor; and/or a chemotherapeutic agent selected from Gemcitabine (Gemzar®), Fluorouracil (5-FU), Capecitabine (Xeloda®), FOLFIRINOX and Nab-paclitaxel (Abraxane®).

Preferably, the pharmaceutical composition for use in the treatment of pancreatic cancer comprises one or more additional therapeutic agents selected Gemcitabine (Gemzar®), Fluorouracil (5-FU) and Nab-paclitaxel (Abraxane®).

In some embodiments, the pharmaceutical composition comprises one or more MEK inhibitors and/or IGF1R inhibitors.

The pharmaceutical composition of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

Depending on the choice of CCR1 antagonist, certain effective formulations are known and commercially available.

The pharmaceutical compositions of the invention may be obtained by conventional procedures using conventional pharmaceutical excipients, known in the art. Thus, pharmaceutical compositions intended for oral use may contain, for example, one or more colouring, sweetening, flavouring and/or preservative agents.

Methods of Prognosis

The invention provides a method of carrying out a prognosis of a subject diagnosed with pancreatic cancer, said method comprising the steps of:

measuring the level of CCR1 expression in a sample taken from the subject;

comparing the level of CCR1 expression measured in step a) with a reference expression level; and determining the subject's prognosis based on the level of CCR1 relative to the reference expression level, as determined in step b);

wherein an increased level of CCR1 expression compared to the reference expression level is indicative of an unfavourable prognosis for the subject; and a decreased or unchanged level of CCR1 expression compared to the control is indicative of a favourable prognosis for the subject.

In another aspect of the present invention, there is provided a method of carrying out a prognosis of a subject diagnosed with pancreatic cancer, said method comprising the steps of:

measuring the level of immune (e.g. macrophage) infiltration in a sample taken from the subject;

comparing the level of immune (e.g. macrophage) infiltration measured in step a) with a reference infiltration level; and determining the subject's prognosis based on the immune (e.g. macrophage) infiltration level compared to the reference infiltration level, as determined in step b);

wherein increased level of immune (e.g. macrophage) infiltration compared to the reference infiltration level is indicative of an unfavourable prognosis for the subject; and a decreased or unchanged level of immune (e.g. macrophage) infiltration compared to the reference infiltration level is indicative of a favourable prognosis for the subject.

For example, both the level of immune (e.g. macrophage) infiltration and CCR1 expression may be measured in the sample taken from the subject.

For example, levels of expression of MYC, a SMAD4 mutation, or a classical Moffitt's tumour RNA subtype may also be measured as part of the prognosis.

According to a further aspect of the present invention, the method of carrying out a prognosis includes measuring an expression level of at least one biomarker selected from PIM3, GSK3B, ATK1, CDK1, CDK5, MAPK14, MTOR, MAPK3, CAMK2A, MAP2K1, MAPK8, PRKACA, SRC, RPS6KA1, MAPK1 and PRKCA.

The method may involve determining a test score derived from the measured expression level of CCR1 and the at least one biomarker and comparing the test score and a pre-determined threshold score, wherein a test score that is greater than the pre-determined threshold score is indicative of an unfavourable prognosis for the subject; and a test score that is less than or equal to the pre-determined threshold score is indicative of a favourable prognosis for the subject.

It will be understood that the term "prognosis" refers to the likely course of a medical condition (e.g. pancreatic cancer). Thus, the term "favourable prognosis" will be understood to mean that the course of the pancreatic cancer will be favourable for the subject. Suitably, the term "favourable prognosis" means that the likelihood of the subject with pancreatic cancer surviving for at least 3 month, preferably for at least 6 month, more preferably for at least 1 year, even more suitably for at least 2 years, and most preferably for at least 5 years, following one or more standard pancreatic cancer treatment regimens (i.e. surgery and/or chemotherapeutic treatment) is high. That is to say, the term "favourable prognosis" refers to a subject with pancreatic cancer who has, within the context of generally very poor prognosis amongst with pancreatic cancer patients, a high likelihood of responding well to one or more standard pancreatic cancer treatment regimens (i.e. a high likelihood that the pancreatic cancer will not recur or progress following treatment).

The term "unfavourable prognosis" will be understood to mean that the course of the pancreatic cancer will be unfavourable for the subject. Suitably, the term "unfavourable prognosis" means that the likelihood of the subject with pancreatic cancer surviving for at least 3 months (suitably for at least 6 months, more suitably for at least 1 year, even more suitably for at least 2 years, and most suitably for at least 5 years) following one or more standard pancreatic cancer treatment regimens (i.e. surgery and/or chemotherapeutic treatment) is low. That is to say, the term "unfavourable prognosis" refers to a subject with pancreatic cancer who has a low likelihood of responding well to one or more standard pancreatic cancer treatment regimens (i.e. a high likelihood that the pancreatic cancer will recur or progress following treatment).

Suitably, the methods of prognosis described hereinabove include an initial step of obtaining a sample from the subject. Said sample may be, for example, a sample of tumour cells taken from the patient's pancreas (or surrounding tissue) and/or a sample of the subject's blood. The sample may be obtained using any suitable technique known in the art, such as, for example, surgery, biopsy or blood sample.

The reference levels mentioned hereinabove (i.e. the "reference expression level" and the "reference infiltration level"), refer to control values that serve as reference points (or benchmarks), from which the levels of CCR1 expression and/or macrophage infiltration measured in the sample taken from the subject may be compared. The reference levels may correspond to, for example, the average level of CCR1 expression and/or the average level of macrophage infiltration in subjects who have not been diagnosed with pancreatic cancer (e.g. a negative control or reference level), or to the average level of CCR1 expression and/or the average level of macrophage infiltration for subjects diagnosed with pancreatic cancer (e.g. a positive control or reference level).

In one embodiment, a gene expression level or macrophage infiltration level in a subject can be stratified into "high", "medium" and "low" groups depending on whether the level falls in the lower quartile, the highest quartile or the middle two quartiles of the relevant population; alternatively, a gene expression level or macrophage infiltration level in a subject can be stratified into "high" or "low" groups depending on whether the level falls in the lower quartile, the highest quartile or the middle two quartiles of the relevant population.

Kits of Parts

As mentioned above, a CCR1 antagonist for use in accordance with the invention is most preferably used in combination with one or more further therapeutic agents. The CCR1 antagonist may therefore be provided together with such other therapeutic agents.

In another aspect of the present invention, there is therefore provided a kit of parts comprising the following components:

- a CCR1 antagonist, as defined herein, or pharmaceutically acceptable salt, solvate or hydrate thereof, optionally in association with a pharmaceutically acceptable adjuvant, diluent or carrier; and
- one or more chemotherapeutic agents selected from Gemcitabine (Gemzar®), Fluorouracil (5-FU), Capecitabine (Xeloda®), FOLFIRINOX and Nab-paclitaxel (Abraxane®), or pharmaceutically acceptable salt, solvate or hydrate thereof, optionally in association with a pharmaceutically acceptable adjuvant, diluent or carrier;

wherein the components are provided in a form which is suitable for sequential, separate and/or simultaneous administration.

In another aspect of the present invention, there is provided a kit of parts comprising the following components:

- a CCR1 antagonist, as defined herein, or pharmaceutically acceptable salt, solvate or hydrate thereof, optionally in association with a pharmaceutically acceptable adjuvant, diluent or carrier; and
- an MEK inhibitor and/or an IGF1R inhibitor, or pharmaceutically acceptable salt, solvate or hydrate thereof, optionally in association with a pharmaceutically acceptable adjuvant, diluent or carrier;

wherein the components are provided in a form which is suitable for sequential, separate and/or simultaneous administration.

In another aspect of the present invention, there is provided a kit of parts comprising the following components:

- a CCR1 antagonist, as defined herein, or pharmaceutically acceptable salt, solvate or hydrate thereof, optionally in association with a pharmaceutically acceptable adjuvant, diluent or carrier;
- an MEK inhibitor and/or an IGF1R inhibitor, or pharmaceutically acceptable salt, solvate or hydrate thereof, optionally in association with a pharmaceutically acceptable adjuvant, diluent or carrier; and
- one or more chemotherapeutic agents selected from Gemcitabine (Gemzar®), Fluorouracil (5-FU), Capecitabine (Xeloda®), FOLFIRINOX and Nab-paclitaxel (Abraxane®), or pharmaceutically acceptable salt, solvate or hydrate thereof, optionally in association with a pharmaceutically acceptable adjuvant, diluent or carrier;

wherein the components are provided in a form which is suitable for sequential, separate and/or simultaneous administration.

In another aspect of the present invention, there is provided a kit of parts comprising the following components:

a CCR1 antagonist, as defined herein, or pharmaceutically acceptable salt, solvate or hydrate thereof, optionally in association with a pharmaceutically acceptable adjuvant, diluent or carrier;

a PD-1 and/or PD-L1 inhibitor, or pharmaceutically acceptable salt, solvate or hydrate thereof, optionally in association with a pharmaceutically acceptable adjuvant, diluent or carrier; and one or more chemotherapeutic agents selected from Gemcitabine (Gemzar®), Fluorouracil (5-FU), Capecitabine (Xeloda®), FOLFIRINOX and Nab-paclitaxel (Abraxane®), or pharmaceutically acceptable salt, solvate or hydrate thereof, optionally in association with a pharmaceutically acceptable adjuvant, diluent or carrier;

wherein the components are provided in a form which is suitable for sequential, separate and/or simultaneous administration.

The kit of parts is for the treatment of pancreatic cancer. Suitably, the kit of parts are for use in a treatment of pancreatic cancer as described herein, and/or for use in the treatment of a subject who has been identified as being suitable for treatment according to a method described herein Features, integers, characteristics, compounds, or properties described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive.

EXAMPLES

Example 1—Macrophage Populations as a Fraction of Immune Infiltrate in Human Pancreatic Cancer ConsensusTME: A Deconvolution Tool ConsensusTME is a deconvolution tool that integrates gene sets from all the other current deconvolution methods for relative tumour microenvironment (TME) cell estimation of 18 cell types. That is to say, ConsensusTME is a package for the R software environment that compiles common cell type specific gene sets used by different published TME cell estimation methods. This program permits the estimation of cell type quantities using bulk expression data of human tumour samples. Furthermore, it includes cell type specific gene markers from independent cell estimation methods, filters gene sets to be specific for different cancer types and uses single sample gene set enrichment analysis (ssGSEA) to compute TME cell type and tumour specific enrichment scores from bulk gene expression data.

To generate the ConsensusTME gene sets, cell types for which there were signatures from at least two different sources were identified; 18 cell types were used in total.

To extract genes from the signature matrix "LM22" used by CIBERSORT (Nature Methods, 2015, 12, 453-457), genes whose expression value was below 1.96 standard deviations of the mean for each cell type were first filtered out. In addition, activated and resting states for corresponding cell types were collapsed. Once signature genes from the other deconvolution methods (Bindea et al., Immunity, 2013, 39(4), 782-795; Danaher et al., Journal for ImmunoTherapy of Cancer, 2017, 5(18), 1-15; Davoli et al., Science, 2017, 355(6322), 2499-250; CIBERSORT, Nature Methods, 2015, 12, 453-457; MCP-Counter, Genome Biology, 2016, 17(218), 1-20; and xCell, Genome Biology, 2017, 18(220), 1-14) had been collected, a unique union of the genes for each cell type was created. From this union of genes, a set of cell type-specific genes was curated for each of the TCGA cancer types. This was done using a similar approach to the TIMER algorithm (Genome Biology, 2016, 17(174), 1-16) where genes were only included if the expression of that gene has a negative correlation (Pearson's correlation<0.2, p-value 0.05) with tumour purity (ABSOLUTE derived) for the corresponding cancer type.

Finally, single-sample gene set enrichment analysis (ssGSEA) was employed to calculate normalised enrichment score (NES) for each cell type as described above. General immune scores for each tumour types were generated by combining the genes of the different immune cells into one gene set for each TCGA cancer type.

To systemically explore the relative contribution of macrophages to the immune infiltrate of tumour samples in pancreatic cancer, gene expression data of TOGA tumour samples were analysed using ConsensusTME to deconvolute immune cell gene expression signatures from each tumour sample bulk RNA mixture, as detailed above.

A comprehensive benchmark dataset consisting of pancancer data (DNA-derived purity, leukocyte methylation and H&E-derived lymphocyte counts) and cell-specific benchmark data sets (peripheral blood cells and tumour tissues) were collected.

Figure 1:
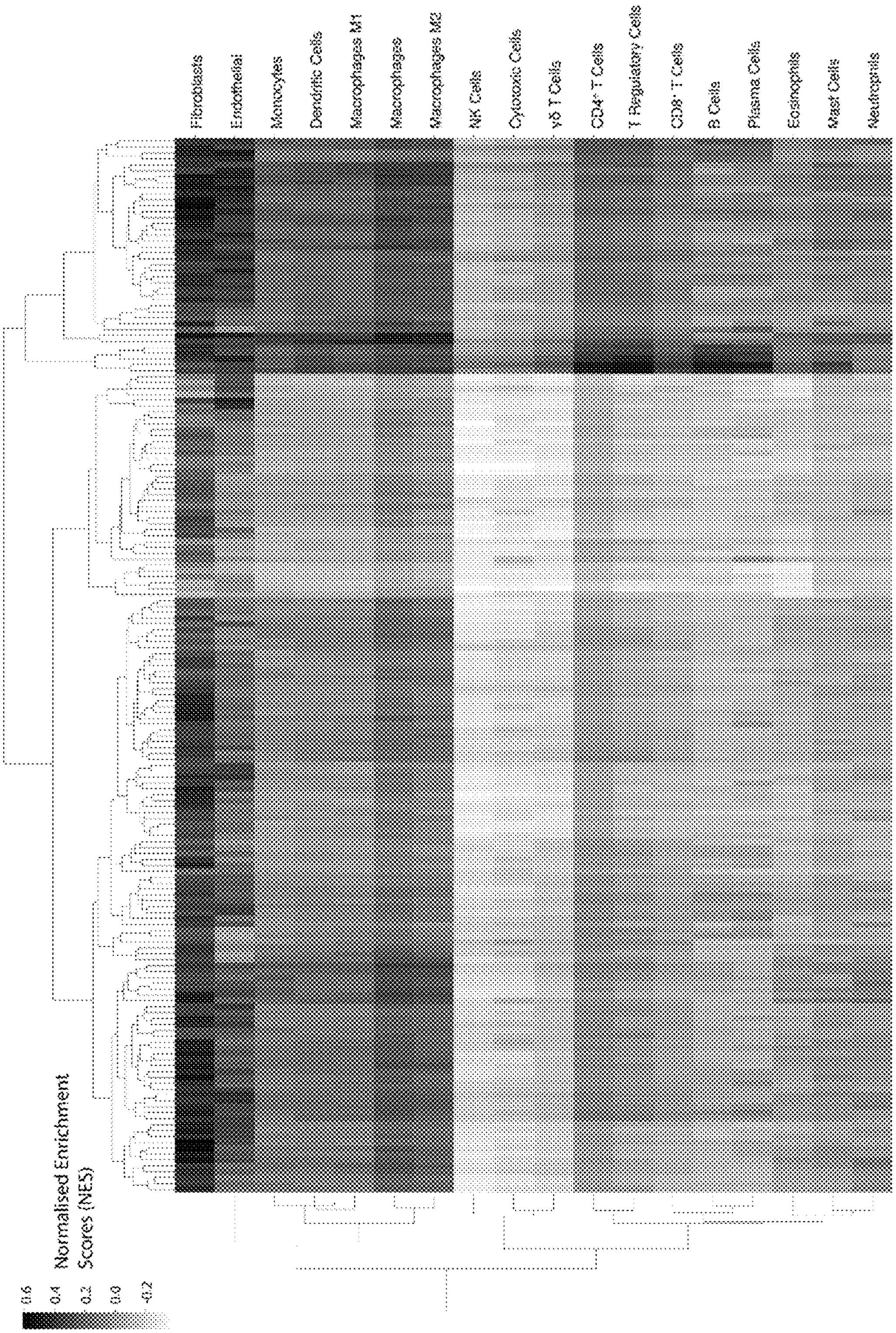
FIG. 1 shows the ssGSEA analysis of immune infiltrate fractions in TOGA human pancreatic cancer. Columns represent individual patients; rows represent various immune cell types.

The ssGSEA analysis of immune infiltrate fractions in TOGA pancreatic cancer is shown in FIG. 1, where it can be seen that macrophages were one of the most abundant immune cell types in the immune infiltrate in pancreatic cancer patients.

Example 2—Kaplan-Meier Survival Analysis of Macrophage Infiltrate in TOGA PAAD (Pancreatic Cancer) for Stratification of Pancreatic Cancer Patients Kaplan-Meier Survival Analysis Using gene expression data from The Cancer Genome Atlas (TOGA), RNA-Seq data collected from cBioPortal, ConsensusTME was applied to estimate the relative abundance of 18 immune cell types for the PAAD cohort. Data was gene expression data from RNA-Seq, which was available publicly at cbioportal.org (Cancer Discovery, 2014, 2(5), 401-404). Patients were initially stratified into "high", "medium" and "low" depending on the abundance of Macrophages (High>0.75 quartile>Medium>0.25 quartile>Low).

A Kaplan-Meier survival analysis of progression free survival based on this stratification showed a bifurcation in survival curves with the high/medium group remaining together while the low group showed better prognosis. With high and medium groups showing no significant difference they were combined to leave two patient groups: macrophage low and macrophage medium/high.

It was found that patients with medium or high numbers of macrophage infiltration correlated well with poor prognosis.

A further KM analysis in TOGA PAAD, stratifying patients by CCR1 expression, revealed patients in with CCR1 high expression (>median) showed significantly worse progression free survival.

The ConsensusTME macrophage gene signature was next combined with CCR1 expression to create a combined signature. ssGSEA was carried out to examine the enrichment of this combined signature and samples were once more stratified into either "Low" or "Medium/High" based upon enrichment of this signature. This revealed the combined signature could predict differences progression free survival (PFS) in pancreatic cancer patients.

Figure 2:
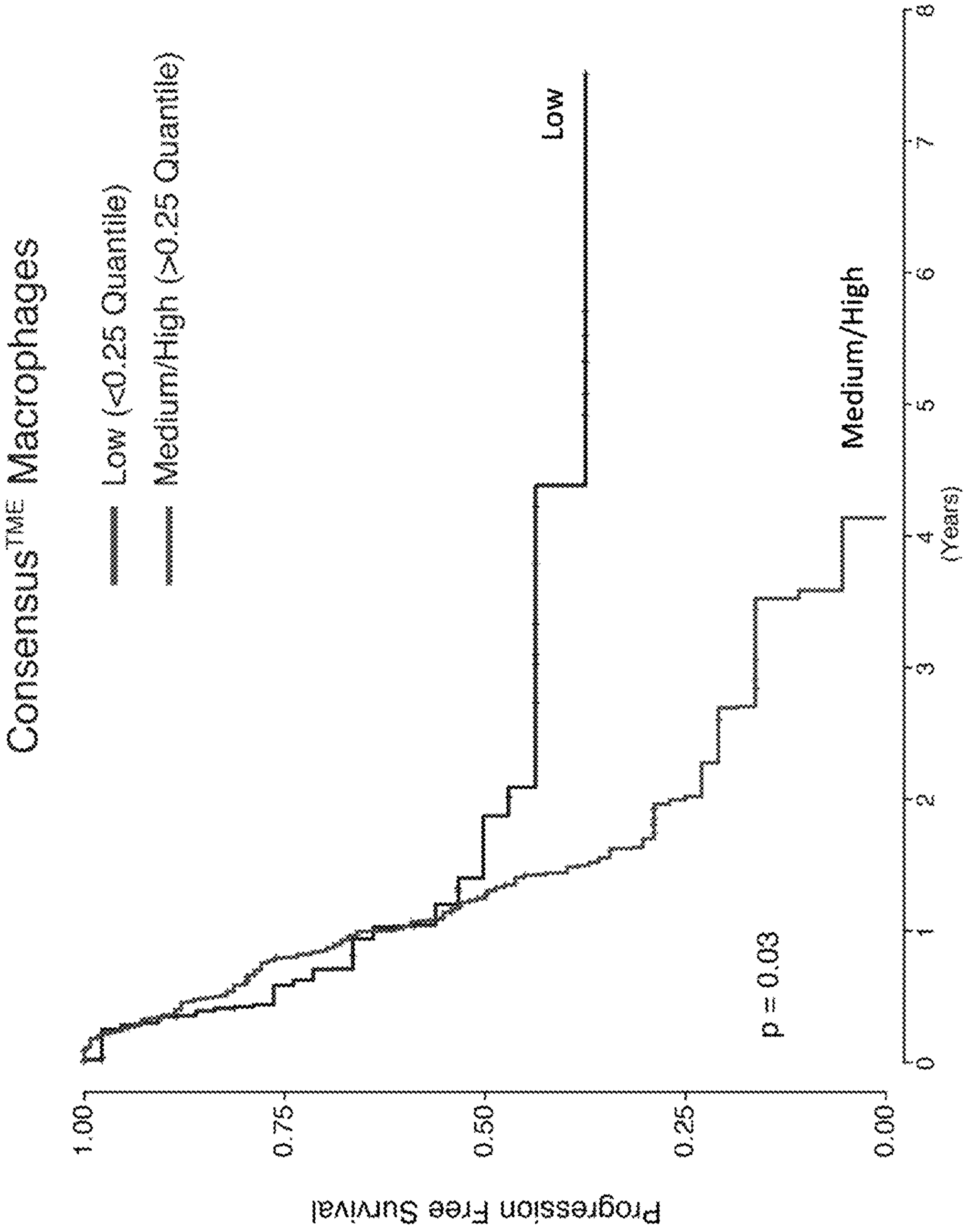
FIG. 2 shows the Kaplan-Meier survival analysis of macrophage infiltrate in TOGA PAAD (pancreatic cancer) for stratification of pancreatic cancer patients. Survival of pancreatic cancer patients calculated by Immune Score versus M1 and M2-like macrophage signatures.

Results are shown in FIG. 2.

Example 3—PDAC Mesenchymal Cells Form Vascular Mimicry in a 3D In Vitro Assay of Invasion Cell Culture The murine cancer cell lines used, TB32048 (hereafter referred to as PDAC epithelial) and K8484 (hereafter referred to as PDAC mesenchymal), were isolated from tumours arising from KPC mice (generated by David Tuveson) and supplied by Duncan Jodrell. All cell lines were grown in Dulbecco's Modified Eagle Medium: Nutrient MixtureF-12, DMEM/F12, (Gibco) supplemented with 10% heat inactivated Fetal Bovine Serum, FBS, (Gibco), incubated at 37° C. in 5% $CO_2$. All cell lines were tested negative for *mycoplasma*.

3D In Vitro Model of Invasion

Cell-matrix cultures were performed by seeding PDAC cells onto wells pre-coated with 1 mg/mL Matrix Growth Factor Reduced Matrigel (Becton Dickinson). To observe cell invasion through Matrigel, plates were placed into IncuCyte Zoom (Essen Bioscience) with the software set to capture images every 3 hours in green and fluorescent protein (GFP/RFP)/Bright Field (or Phase Contrast).

Quantification of VM-Like Structures

To quantify the ability of PDAC cells to form vascular mimicry (VM) structures, 3D in vitro assays were quantified by Angiogenesis analysis software provided by Essen Bioscience. The Angiogenesis tool allows for the automated and objective quantification of the number of branches a 3D structure has in a representative field. Once parameters were defined, they were applied to all 3D in vitro structure formation experiments for robust and reproducible quantification.

The results are shown in FIG. 3.

In contrast to PDAC epithelial cells forming clusters in a 3D in vitro assay of invasion, the PDAC mesenchymal cells formed extensive and complex tubular, latticed networks across the entire surface area of the well. The integrity of these networks was largely unchanged over the duration of the experiment. Additionally, the tubular structures have been suggested to represent VM, and hints that (epithelial-to-mesenchymal transition) EMT status can mediate the ability to form structures in 3D architecture.

Example 4—Primary BMDM Impart a Pro-Invasive Phenotype to Pancreatic Cancer Cells, Irrespective of EMT Status ZsGreen-labelled primary BMDM were co-cultured with mCherry-expressing PDAC epithelial cells in a 3D in vitro model of invasion to best represent a biologically relevant macrophage population in all subsequent macrophage co-culture assays.

Bone Marrow-Derived Macrophages

Bone marrow was isolated from the femur and tibia of C57BL/6 mice, 10 to 14 weeks of age. Femurs and tibias were flushed with PBS buffer, passed through a 70 μM sieve (Greiner Bio-One), and cells were reseeded onto standard plastic tissue culture 100 $mm^2$ dishes (Corning). Cells were differentiated into bone marrow derived macrophages (BMDM) by culture in DMEM/F12 medium supplemented with 10% FBS and 15% L929-Cell Conditioned Media (LCM), incubated at 37° C. in hypoxic conditions (1% $O_2$) for 3 days. BMDM were grown and maintained in Dulbecco's Modified Eagle Medium: Nutrient Mixture F-12, DMEM/F12, (Gibco) supplemented with 10% heat-inactivated Fetal Bovine Serum, FBS, (Gibco), incubated at 37° C. in 1% 02.

Cell Co-Cultures

Culture conditions for PDAC and BMDM cell lines used in this study are described above. For co-cultures, mCherry-labelled PDAC cells were mixed 1:1 with ZsGreen-labelled macrophages, typically primary BMDM unless otherwise noted. Co-cultures were seeded and kept as subconfluent cultures for 48-96 hours in either 2D or 3D conditions.

Quantification of 3D In Vitro Assays of Invasion

To quantify the invasive capacity of PDAC cells, 3D in vitro invasion assays were quantified using software provided by Essen Bioscience, NeuroTrack. This method employs software algorithms designed by Essen Bioscience to measure kinetic data generated by the IncuCyte Zoom platform. Unlike high-content imaging systems, which require fixation, staining, and endpoint analysis of cells, the algorithm measured live-cell dynamics. NeuroTrack displayed the number of cells invading out of 3D structures against time. This method allowed for the exclusion of macrophages (non-labelled and/or ZsGreen) in the counting process of co-cultures with mCherry-labelled PDAC cells. Once parameters were defined, they were applied to all 3D in vitro invasion assays for quantification.

The NeuroTrack software measures fluorescent-labelled cells. The processing definitions were tailored to consistently analyse the invasion of two PDAC cell types (both are nuclear labelled by H2B-mCherry), regardless of epithelial-mesenchymal transition (EMT) status and 3D structure dimensions. Here, BMDM represents ZsGreen-labelled cells. In this method, only PDAC cells that have invaded out of 3D structures are counted if they have a fluorescent mCherry label present in their nucleus. Data is plotted with number of nuclei counted on the y-axis and time on the x-axis.

The results are shown in FIG. 4.

Instead of forming vascular networks, the PDAC epithelial cells first formed their respective rounded, clumped clusters within 24 hours of seeding before, surprisingly, invading out of these structures around the 96-hour time point. Once free, these invasive cells proceeded to spread and covered the entire surface area of the plate after approximately 7 days. The behaviour of PDAC mesenchymal cells alone or in the presence of BMDM was also examined in a parallel study. PDAC mesenchymal cells were also found to first form their VM structures within 24 hours of seeding prior to breaking free and exhibiting a pro-invasive phenotype, albeit at a much quicker rate, at around the 48-hour time point.

Example 5—Multi-Omics Approach to Identify Novel RNA Targets (Transcriptome) that Promote PDAC Cell Invasion Following Prolonged Co-Culture with BMDM To elucidate changes in the transcriptome of PDAC cells and macrophages following prolonged co-culture, pre-educated PDAC epithelial and mesenchymal cells from co-cultures with BMDM were sorted by Fluorescence-activated cell sorting (FACS), along with mono-culture PDAC cells and BMDM controls, and submitted for RNA-sequencing. Genome-wide transcriptomic analysis from co-culture of PDAC cells compared to mono-culture demonstrated upregulation of nearly all chemokine receptor and their receptor genes.

RNA Quality Control

RNA quality was checked using the Bioanalyzer/RNA nano 6000 kit (Agilent).

Determining Differentially Expressed Genes

Non-specific filtering was used to remove genes with an interquartile range less than 0.3 or with low expression values (less than 3 on log 2 scale) in 90% or more of the samples. To find differentially expressed genes (DEGs) after co-culture compared to monoculture in PDAC cells, thresholds were set for minimal fold change of 1.5, and median false discovery rate (FDR) of 0.10. These same parameters were used to determine DEGs in BMDM monoculture versus co-culture, and in other relevant comparisons. Unannotated transcripts were not considered.

qRT-PCR Gene Expression Analysis

Total RNA was isolated and purified from cells using Qiazol reagent and miRNeasy mini kit (Qiagen). cDNA was synthesized using the High Capacity RNA-to-cDNA kit (ABI) according to manufacturer's instructions. qRT-PCR was performed using Power SYBR Green PCR Master Mix (ABI) on the TaqMan 7900 (ABI). Relative expression levels were defined using the ΔΔCt method and normalizing to 18S rRNA and/or GAPDH.

The results are shown in FIG. 5.

Macrophage-mediated induction of chemokine family genes was observed in all PDAC cells tested, irrespective of EMT status, and confirmed by quantitative real-time polymerase chain reaction (qRT-PCR).

Example 6—Multi-Omics Approach to Identify Novel Protein Targets (Proteome) that Promote PDAC Cell Invasion Following Prolonged Co-Culture with BMDM To elucidate changes in the proteome or secretome of PDAC cells and macrophages following prolonged co-culture, pre-educated PDAC epithelial and mesenchymal cells from co-cultures with BMDM were harvested in bulk, along with mono-culture PDAC cells and BMDM controls, and submitted for TMT-full proteome and secretome analysis.

CTAP-Labelling

For exchange-of-label experiments, PDAC and BMDM cells were first metabolically labelled by growth for at least ten cellular doublings (ten or more days) in 1-arginine and 10% dialyzed FBS-containing SILAC DMEM supplemented with 798 μM light isotope-labelled 1-lysine (hereafter referred to as Light or DAP) or heavy isotope-labelled [$^{13}C_6$,$^{15}N_2$]l-lysine (+8 daltons; Cambridge Isotopes); (hereafter referred to as Heavy or d-Lys-8). For experiments that maintained the label, cells were initially grown for at least ten cellular doublings (ten or more days) in their respective precursors: DOPA decarboxylase (DDC) expressing cells (Primary BMDM) in DAP (L) and lyr-expressing cells (PDAC cells) in d-lysine (H). Populations were then combined in 10 mM DAP (L) and 1 mM d-lysine (H) and grown together for 4 days (approximately four cellular doublings) in co-culture. Co-cultures were seeded at ratios in which an equal number of cells were expected at the end of the experiment. Conditioned media (CM) was harvested and snap frozen for downstream secretome analysis. Cell pellets and lysate were harvested and snap frozen for downstream proteome analysis.

The results are shown in FIGS. 6 and 7.

Proteomic analysis from PDAC cells in co-culture compared to mono-culture corroborate RNA-sequencing data suggesting PDAC cells adopt macrophage-derived chemokines following prolonged co-culture with BMDM.

Example 7—Multi-Omics Approach to Identify Novel Protein Targets (Secretome) that Promote PDAC Cell Invasion Following Prolonged Co-Culture with BMDM It was postulated that the rapid pro-invasive phenotype changes observed in 3D admixed cultures were likely mediated by signals released from those PDAC epithelial and BMDM cell interactions. To identify them, conditioned media (CM) was harvested from 48 hour incubated co-cultures and the protein extracts used to interrogate an inflammation antibody array.

Conditioned Media

Conditioned media samples were isolated from PDAC and BMDM mono- and co-cultures 48 hours post-seeding and incubated on a mouse inflammation antibody array (Abcam) according to manufacturer instructions. Images were acquired and the intensity of the signals were analysed using Amersham Imager 680.

The results are shown in FIGS. 8 and 9.

Of 40 potential candidates, the three inflammatory signals with highest detectably upregulated intensities by prolonged co-culture included the chemokines CCL2, CCL3 and CCL9; ligands for C—C Motif Chemokine Receptor 1 (CCR1).

Example 8—CCR1 Blockade Inhibits Macrophage-Mediated Pro-Invasive Phenotype

As upregulation of CCR1 expression in PDAC cells following prolonged co-culture with BMDM was confirmed by qRT-PCR and flow cytometry, it was next sought to determine whether blockade of CCR1 using various small molecule inhibitors could potentially disrupt the crosstalk between PDAC cells and macrophages that enables BMDM to impart a pro-invasive phenotype to PDAC cells in a 3D in vitro assay of invasion.

CCR1 Antagonist Treatment in Cell Co-Cultures

Pre-treatment: PDAC cells and BMDM were pre-treated with CCR1 antagonists 24 hours prior to the start of the experiment, harvested and then seeded according to the co-culture method previously described for the duration of the experiment.

Treatment at time of co-culture: PDAC cells and BMDM were seeded according to the co-culture method as previously described and CCR1 antagonists were treated at the time of seeding and allowed to incubate for the duration of the experiment.

The results are shown in FIGS. 10 to 13.

Treatment with three commercially available CCR1 antagonists (BX-471, J113863 and UCB35625, all sourced from Tocris Bioscience) demonstrated a striking ability to rein in the effect of macrophages to confer functional pro-invasive abilities to PDAC cells while also blunting the induction of CCR1 expression due to prolonged co-culture by qRT-PCR and flow cytometry.

Example 9—Knockdown of CCR1 by siRNA Blunts Macrophage-Mediated Pro-Invasive Phenotype Gene Targeting and Expression Gene knockdown by siRNA was accomplished using SmartPool siRNAs (Thermo Fisher Scientific) or individual siRNA sequences and transfected using 15 nM siRNA and RNA iMAX (Invitrogen) transfection reagent.

siRNA Knockdown of CCR1 in Cell Co-Cultures siRNA knockdown of CCR1 was performed on PDAC cells and BMDM 24 hours prior to the start of the experiment, harvested and then seeded according to the co-culture method previously described for the duration of the experiment.

The results are shown in FIGS. 14 and 15.

Knockdown of CCR1 in PDAC and BMDM cells prior to co-culture depressed induction of CCR1 expression compared to control and also partially inhibited macrophage-mediated invasion in 3D, a result observed with multiple different siRNAs targeting CCR1.

Example 10—Neutralising Antibodies to Ligands that Bind to CCR1 can Moderate Macrophage-Mediated Pro-Invasive Phenotype Inflammatory chemokine receptors display promiscuous ligand binding, and the chemokines in turn bind to multiple different chemokine receptors. The extent to which this represents biological redundancy or whether there are discrete signals triggered by different chemokines through individual chemokine receptors remains to be determined. Two known ligands were neutralised, CCL3 and CCL9 (human homolog CCL15), and one unknown but potentially novel ligand, IL-1B, of CCR1 by use of neutralising antibodies (all; R&D Systems) to test whether the blockade of a single ligand might be sufficient to diminish the pro-invasive phenotype conferred by macrophages to PDAC cells. All ligands were chosen after being identified and corroborated in the previous multi-omics high-throughput screen.

Neutralising Antibody Treatment in Cell Co-Cultures

Pre-treatment: PDAC cells and BMDM were pre-treated with CCR1 ligand neutralising antibodies 24 hours prior to the start of the experiment, harvested and then seeded according to the co-culture method previously described for the duration of the experiment.

Treatment at co-culture: PDAC cells and BMDM were seeded according to the co-culture method as previously described and CCR1 ligand neutralising antibodies (sourced from R&D Systems) were treated at the time of seeding and allowed to incubate for the duration of the experiment.

The results are shown in FIG. 16.

Single blockade of each of the three ligands (CCL3 and CCL9 and IL-1B) demonstrated efficacy in preventing PDAC cells from invading out of their structures in the presence of BMDM. Interestingly, anti-CCL9 was unique in its ability for observed macrophage migration with loss in tracking ability of PDAC cells for invasion. This suggests a distinct dichotomy in how the various ligands may bind to CCR1 and provides rationale for further investigation. Importantly, IL-1B was observed to also dull the PDAC pro-invasive phenotype.

Example 11—CCR1 Antagonist, BX471, Blunts Primary Tumour Growth In Vivo

A subcutaneous flank injection model was used as a pilot and surrogate experiment of a genetically engineered mouse model of PDAC, KPC mouse model. Here, PDAC cell lines with or without BMDM were injected and primary tumours tracked for growth.

In Vivo Mouse Studies

Pre-Treatment: PDAC and BMDM cells were pre-treated with CCR1 antagonist, BX471, 24 hours prior to the start of the experiment and seeded according to the co-culture method previously described for overnight incubation. The next day, $1\times10^6$ mCherry-labelled PDAC mesenchymal cells with and without an equal number of primary BMDM were injected with Matrigel into the flanks of 6 to 8 weeks of age male immune competent C57BL/6J mice (sourced from Charles River Laboratories). Starting at day 7, mice were independently measured using calipers.

The results are shown in FIGS. 17 and 18.

Reduced primary tumour growth was observed in the treatment arm of CCR1 antagonist, BX471. Importantly, BX471-treated mice were observed to have a prolonged overall survival especially when PDAC cells were combined with BMDM cells.

Example 12—High Expression of CCR1 is Associated with Macrophage Infiltration and can be Used to Stratify Patients with Pancreatic Cancer Consensus TME: A Deconvolution Tool To extract genes from the signature matrix "LM22" used by CIBERSORT, genes whose expression value was below 1.96 standard deviations of the mean for each cell type were first filtered out. In addition, activated and resting states for corresponding cell types were collapsed. Once signature genes from the other deconvolution methods (Bindea et al., Danaher et al., Davoli et al. CIBERSORT, MCP-Counter and xCell) had been collected, a unique union of the genes for each cell type was created. From this union of genes, a set of cell type-specific genes was curated for each of the TCGA cancer types. This was done using a similar approach to the TIMER algorithm where genes were only included if the expression of that gene has a negative correlation (Pearson's correlation<0.2, p-value 0.05) with tumour purity (ABSOLUTE derived) for the corresponding cancer type. Finally, single-sample gene set enrichment analysis (ssGSEA) was employed to calculate normalised enrichment score (NES) for each cell type as described above. General immune scores for each tumour types were generated by combining the genes of the different immune cells into one gene set for each TCGA cancer type.

ConsensusTME Cell Type Comparisons

ConsensusTME cell type abundances were generated using bulk tumour RNA-Seq from the TCGA pancreatic cancer cohort as previously described. ssGSEA enrichment scores for each cell type were further normalised by dividing by the total immune cell abundance to better allow comparisons of cell type scores resembling fractional proportions of the total immune cell infiltrate. These scores were then used to stratify samples into those with a high fraction of immune cells vs low using a median split.

Kaplan-Meier Survival Analysis

Using TCGA expression data of Example 2, Kaplan-Meier survival analysis was performed as previously described.

RNA-Seq data from the TOGA pancreatic cancer cohort was used for Kaplan-Meier analysis. Patients were stratified into "Low" or "High" expression based on a medium split. A log-rank test between the two groups showed the CCR1 low group to have significantly better progression free survival than the high group (p=0.031).

Using immune cell estimates generated by ConsensusTME it can be seen that the samples in the Macrophage, Dendritic cell & Monocyte high category have a higher mean expression of CCR1 than the immune cell low category. The inverse is seen for many other immune cell types including CD8+ T cells, B cells and T regulatory cells. This shows there is a significant association between CCR1 and macrophage infiltration in TOGA pancreatic cancer samples.

Patients with high expression of CCR1 gene expression show worse progression free survival than those with low levels.

The results are shown in FIGS. 19 and 20.

Example 13—Gene Ontology (GO) Analysis of the Most Changed Proteins Following Prolonged Co-Culture Reveals Enrichment of Chemokine Related Biological Processes Gene Ontology (GO) analysis of the most changed proteins following prolonged co-culture (as described hereinabove, Example 4) reveals enrichment of chemokine related biological processes Gene Ontology (GO) provides a system for hierarchically classifying genes or gene products into terms organised in a graph structure. One of the main uses of GO is to perform enrichment analysis on gene sets. For example, given a set of genes that are upregulated in pancreatic cancer cells under prolonged co-culture conditions with BMDM, this enrichment analysis found GO terms, or biological processes, that are over-represented using annotations for that gene set.

Using the PANTHER Classification System (pantherdb.org), the names of the genes to be analysed were input, one per row or separated by a comma. The tool can handle both MOD specific gene names and UniProt IDs. Selection the GO aspect (molecular function, biological process, cellular component) for analysis was made (in this instance, biological process). Species selection, both mouse and human, was considered and analysed. Results are displayed on a redirected PANTHER website. These results are based on enrichment relative the set of all protein-coding genes in the genome selected in step 3.

The results are shown in FIG. 21.

Example 14—a Combined Macrophage and CCR1 Signature can be Used to Stratify Pancreatic Cancer Patients by Progression Free Survival Kaplan-Meier Analysis A combined gene signature was created by combining the ConsensusTME macrophage gene signature with CCR1 to create a new gene set before using ssGSEA to generate normalised enrichment scores for the new gene set in the TOGA pancreatic cancer cohort. The stratification for the combined signature was carried out as previously described in the macrophage signature Kaplan-Meier analysis to create the "Medium/High" (x>0.25 quantile) and "Low" (x<0.25 quantile) categories. The log-rank test showed enrichment of this combined signature was associated with significantly worse progression free survival (p=0.03).

To examine the combined effects of macrophage infiltration and high levels of CCR1 expression within a tumour a combined gene signature of ConsensusTME macrophages and CCR1 expression was created. Using ssGSEA to determine enrichment of this score across patients in the pancreatic cancer TOGA cohort it was observed that enrichment of the combined signature was indicative of a worse prognosis. This combined signature could be used in place of two separate Kaplan-Meier analyses to help further stratify patients.

The results are shown in FIG. 22.

Example 17—Treatment with BX-471 Blunts Activation of Downstream IGF1 Signalling Pathway Genes Western Blotting PDAC cell lines growing in 6-well plates, were treated with recombinant IGF1, CCR1 antagonists, BX-471 or J-113863, or the combination of recombinant IGF1 and CCR1 antagonist for 24 hours. Cells were scraped and lysed in ice-cold lysis buffer containing phosphatase and protease inhibitor cocktails (Roche). The protein extracts were denatured in a heat block for 5 min at 95 C and then resolved by SDS-PAGE. Proteins were transferred to nitrocellulose membranes which were probed with primary antibodies overnight at 4 C, followed by incubation with IRDye secondary antibodies (Li-Cor Biosciences) at room temperature for 60 min. Target proteins were detected with Li-Cor Odyssey Infrared Imaging System. Primary antibodies used include those against AKT, Phospho-AKT, 4E-BP1, Phospho-4E-BP1, MEK, Phospho-MEK, MAPK, Phospho-ERK1/2 and GAPDH (Cell Signalling)

It is evident from previous reports that IGF1 plays a central role in pancreatic cancer resistance to chemotherapy. In this regard, we sought to determine whether CCR1 inhibition influenced the IGF1 signalling pathway in any respect. The expression of downstream IGF1 signalling pathway genes in PDAC cell lines following treatment with recombinant IGF1 and various CCR1 antagonists were assessed with western blotting. The activation and expression profiles of AKT and 4E-BP1 following recombinant IGF1 treatment were particularly blunted by the inhibition of CCR1 using the antagonist BX-471, providing rationale for our preference for BX-471.

To further interrogate how CCR1 inhibition influences the IGF1 signalling pathway, PDAC cell lines following treatment with recombinant IGF1 and various CCR1 antagonists were assessed by comprehensive and comparative proteome and phosphoproteome profiling assays. Data were input into a gene pathway network analysis pipeline developed in house by a postdoctoral scholar in the lab. IGF1 family genes were upregulated with the addition of recombinant IGF1 compared to control. Treatment with CCR1 antagonist, BX-471, however, severely blunted this upregulation.

The results are shown in FIGS. 23 and 24.

Example 18—Treatment with CCR1 Antagonist-Based Combination Therapies is Effective in an In Vivo, Genetically Engineered Mouse Model of PDAC (KPC Model)

Rationale of the In Vivo Study

This study aims to test the combinatorial use of a CCR1 inhibitor with gemcitabine and/or immunotherapy as a novel therapeutic option for PDAC. Preliminary preclinical data provides evidence that small molecule CCR1 inhibitors disrupt the intercellular communication between tumour cells and macrophages, a major subpopulation of the tumour microenvironment implicated as being immune suppressive. As PDAC is characterised by desmoplasia, targeting the tumour microenvironment of patients by first using a CCR1 inhibitor such as BX-471 and then treating the tumours with gemcitabine and/or immunotherapy would be expected to improve upon standards of care and inform future treatment options for PDAC in the clinic. This ongoing proof-of-concept study uses an in vivo KPC mouse model, which is the gold standard, preclinically, to determine the efficacy of therapeutic options for PDAC prior to clinical Phase I consideration. The study includes a randomised, 5-arm intervention study, using KPC Band A mice that are considered clinical grade, as well as additional pilot experiments.

Methods: Animal Model and Sample Processing

The generation of LSL-KrasG12D/+; LSL-Trp53R172H/+; Pdx-1-Cre (KPC) mice bearing spontaneous PDAC has been described previously (Hingorani et al., Cancer Cell, 2005, 7(5), 469-483). Genotyped KPC mice were enrolled in the main intervention study and additional pilot experiments. (Their PC littermates do not generate tumours.) All the KPC experimental groups were randomized for sex and age.

PDAC tumours in KPC mice were detected by palpation and high-resolution ultrasound scans (Vevo 2100, VisualSonics), and confirmed at necropsy. Clinical grade KPC Band A mice, defined as weight-stable, PDAC-bearing mice with tumours with diameters between 3-6 mm (by ultrasound), were enrolled in the main intervention study. KPC Band B mice (non-clinical grade KPC tumour-bearing mice), defined as including (1) identification of more than 1 tumour, (2) large obstructed common bile duct, (3) a tumour larger then 6 mm, (4) presence of nephritis, (5) splenomegaly, (6) large cysts, or (7) visible metastatic tumours present in the diaphragm, were used for additional, initial pilot experiments. All tumours were confirmed histopathologically as adenocarcinomas. All mice were monitored for body weight and condition on a daily basis.

Euthanasia was performed within the 12-hour light period. Terminal bleeds were obtained through exsanguination via cardiac puncture under isofluorane anaesthesia and death was confirmed by cervical dislocation. Plasma was prepared by centrifugation at 14,000 g for 5 minutes at 4 C and snap frozen in liquid nitrogen. Organs, other tissues and aliquots of tumours samples were rapidly dissected in a consistent order and were fixed in 10% neutral buffered formaldehyde (NBF) for 24 hours at room temperature before being transferred to 70% ethanol and processed for immunohistochemistry.

Design of the Main Intervention Study

FIG. 25 shows the experimental plan for the main intervention study, including definitions of the five experimental cohorts used, as well as a timeline showing treatment conditions and study length. The CCR1 inhibitor used was BX-471. The anti PD-1 antibody used was the BioXCell InVivoMab rat anti-mouse PD-1 (CD279) (clone—RMP1-14 monoclonal antibody, IgG2a, k).

Initial Pilot Experiments Reveal Collagen Fragmentation and Increased Immune Cell Infiltration in Combinatorial (3×) Therapy The distinction between hot, altered (excluded and immunosuppressed) and cold tumours is based on the cytotoxic T cell landscape within a tumour. This simplification reflects the outcome of a complex interplay between the tumour and the immune system. KPC Band B mice were used to gain a first look into the various intervention arms of the main study.

A small number of KPC Band B mice were enrolled for either: treatment with vehicle alone, BX-471 alone (FIG. 28A); gemcitabine alone or in combination with BX-471 (FIG. 28B); or as a combinatorial (3× therapy) with gemcitabine, BX-471 and anti-PD1 (FIG. 28C). Due to regulatory restrictions, these mice could not be kept for a prolonged survival study and were culled approximately 10 days after enrolment.

Results of the pilot experiments are shown in FIG. 26. (A) shows immunofluorescence staining of CoIVI (collagen) and KRT19 (tumour cells) in KPC Band B tumours when treated with vehicle or BX-471 for 10 days. (B) shows H&E staining of KPC Band B tumours when treated with either gemcitabine+vehicle or gemcitabine+BX-471 (2× therapy) for 10 days. (C) shows immunofluorescence staining of CD45 (immune cells), CoIVI (collagen) and KRT19 (tumour cells) in KPC Band B tumours when treated with either vehicle or gemcitabine+BX-471+anti-PD-1 (3× therapy) for 10 days.

The characterisation of PDAC stroma as a simple biophysical impediment to drug delivery oversimplifies the contributions of the dozens of distinct cell types that reside in the stroma. Interestingly, however, preliminary analyses of the Band B tumours stained with an antibody against collagen VI revealed altered morphology of the PDAC tumour microenvironment when mice were treated with CCR1 antagonist, BX-471, compared with vehicle control (FIG. 28A). This fragmentation of collagen deposition suggests that impairing the CCR1 signalling axis in mice can produce profound biological architecture changes.

A separate cohort of mice was treated with gemcitabine alone or in combination with BX-471. Interestingly, the H&E stain builds upon the previously observed stromal fragmentation phenotype and indicates increased infiltrating lymphocytes and leukocytes into the primary tumour site (FIG. 28B). The dichotomous difference in infiltrating immune cell populations and fibrotic architecture is striking, suggesting blockade of CCR1 improves immune cell entry into the tumour site.

Finally, one KPC Band B mouse was enrolled for a triple combination therapy, run in parallel with a vehicle control. The triple therapy demonstrated collagen fragmentation (revealed by collagen VI stain), an increase in CD45+ staining, and a decrease in KRT19 tumour cells staining (C).

Initial Results of the Intervention Study: CCR1 Inhibition in Combinatorial 2× (BX-471+GEM) or 3× (BX-471+GEM+Anti-PD1) Therapy Demonstrates Survival Benefit in a Murine Model of PDAC The rationale of the combinatorial therapy arms is for CCR1 inhibition to block the communication between tumour cells and macrophages, fragment the biophysical density of collagen disposition and allow for the influx of TILs into the primary tumour site. Concurrent with CCR1 blockade, treatment of gemcitabine will act to provide systemic and direct tumour kill (double therapy). Finally, addition of antibodies that bind to PD-1 aims to boost the activity of immune cells by stopping this checkpoint molecule from switching off the infiltrating cytotoxic T cells (triple therapy).

FIG. 27 shows survivorship curves for mice enrolled in all 5 treatment arms of the main intervention study. Increased survival was observed for both the 2× (BX-471+gemcitabine) and 3× (BX-471+gemcitabine+anti-PD1) combination treatments compared to gemcitabine or BX-471 single therapies.

While specific embodiments of the invention have been described for the purpose of reference and illustration, various modifications will be apparent to a person skilled in the art without departing from the scope of the invention as defined by the appended claims.

The invention claimed is:

1. A method of treating pancreatic cancer in a subject in need of such treatment, said method comprising administering to said subject a therapeutically effective amount of a CCR1 antagonist, or a pharmaceutically acceptable salt, solvate or hydrate thereof;

wherein the CCR1 antagonist or pharmaceutically acceptable salt, solvate or hydrate thereof is administered to the subject in combination with one or more further therapeutic agents effective as anti-tumour agents in the treatment of pancreatic cancer; and wherein the CCR1 antagonist or pharmaceutically acceptable salt, solvate or hydrate thereof is administered to the subject in combination with a chemotherapeutic agent selected from Gemcitabine, Fluorouracil (5-FU), Capecitabine, FOLFIRINOX (Leucovorin Calcium, Fluorouracil, Irinotecan Hydrochloride and Oxaliplatin), Nab-paclitaxel (Abraxane®) and combinations thereof.

2. The method according to claim 1, wherein the CCR1 antagonist or pharmaceutically acceptable salt, solvate or hydrate thereof is administered to the subject in combination with an immuno-oncology agent (e.g. a PD-1 inhibitor and/or a PD-L1 inhibitor).

3. The method according to claim 1, wherein the CCR1 antagonist or pharmaceutically acceptable salt, solvate or hydrate thereof is administered to the subject in combination with an MEK inhibitor and/or an IGF1R inhibitor.

4. The method according to claim 1, wherein the CCR1 antagonist is selected from UCB-35625, BX-471, AZD-4818, J113863, BAY-865047, BMS-817399, C-4462, CCX-354, CP-481715, and MLN-3897, or a pharmaceutically acceptable salt, hydrate or solvate thereof.

5. The method according to claim 4, wherein the CCR1 antagonist is BX-471 and it is administered to the subject in combination with Gemcitabine and optionally a PD-1 inhibitor.

6. The method according to claim 1, wherein the pancreatic cancer is a stage III or IV cancer and/or wherein the pancreatic cancer is a Pancreatic ductal adenocarcinoma (PDAC).

7. The method according to claim 4, wherein the CCR antagonist is BX-471.

* * * * *